United States Patent
Okochi

(10) Patent No.: US 8,293,933 B2
(45) Date of Patent: Oct. 23, 2012

(54) METHOD OF PRODUCING SUBSTANCE IMMOBILIZING CARRIER

(75) Inventor: Norihiko Okochi, Tokyo (JP)

(73) Assignee: Dai Nippon Printing Co., Ltd., Tokyo (JP)

( * ) Notice: Subject to any disclaimer, the term of this patent is extended or adjusted under 35 U.S.C. 154(b) by 840 days.

(21) Appl. No.: 12/327,835

(22) Filed: Dec. 4, 2008

(65) Prior Publication Data
US 2009/0149667 A1    Jun. 11, 2009

(30) Foreign Application Priority Data
Dec. 5, 2007   (JP) ................................. 2007-315126

(51) Int. Cl.
C07F 7/04   (2006.01)
C07F 7/08   (2006.01)

(52) U.S. Cl. ........................................ 556/419; 556/437

(58) Field of Classification Search ........................ None
See application file for complete search history.

(56) References Cited

U.S. PATENT DOCUMENTS

| | | | |
|---|---|---|---|
| 6,033,784 | A | 3/2000 | Jacobsen et al. |
| 2003/0012734 | A1* | 1/2003 | Pathak et al. ................... 424/9.6 |
| 2003/0087325 | A1* | 5/2003 | Khayyami .................... 435/7.92 |
| 2006/0211137 | A1 | 9/2006 | Ezoe et al. |
| 2007/0181503 | A1 | 8/2007 | Maeno et al. |
| 2007/0190541 | A1 | 8/2007 | Park et al. |

FOREIGN PATENT DOCUMENTS

| | | |
|---|---|---|
| JP | 07-59567 A | 3/1995 |
| JP | 9-309904 A | 12/1997 |
| JP | 11-209680 A | 8/1999 |
| JP | 2000-309745 A | 11/2000 |
| JP | 2005-092198 A | 4/2005 |
| JP | 2006-007204 A | 1/2006 |
| JP | 2006-234758 A | 9/2006 |
| JP | 2007-171180 A | 7/2007 |

OTHER PUBLICATIONS

English translation of Yokota et al. (JP 07059567).*

(Continued)

Primary Examiner — Susanna Moore
Assistant Examiner — Jennifer C Sawyer
(74) Attorney, Agent, or Firm — Sughrue Mion, PLLC

(57) ABSTRACT

The object of the present invention is to inexpensively produce a carrier having a hydrophilic spacer, for immobilizing biological materials, etc., which has been very expensive so far. The present invention relates to a method of producing a substance immobilizing carrier, in which carboxyl groups or active ester groups are positioned on a support, which is characterized by including: a functional group-introducing step in which a functional group is introduced on a surface of a support; a hydrophilic compound binding step in which a hydrophilic compound having a binding group that can bind with the functional group and a hydroxyl group, is bound to the functional group through binding between the functional group and the binding group; a carboxyl group-forming step in which a carboxyl group is formed through ring-opening half-esterification between a cyclic acid anhydride and a hydroxyl group on the bound hydrophilic compound; and, if necessary, an active esterification step in which the carboxyl group formed in the carboxyl group forming step is converted into an active ester.

9 Claims, 10 Drawing Sheets

OTHER PUBLICATIONS

Suman Lata, et al.; "Stable and Functional Immobilization of Histidine-Tagged Proteins via Multivalent Chelator Headgroups on a Molecular Poly(ethylene glycol) Brush"; Analytical Chemistry; Feb. 15, 2005; pp. 1096-1105; vol. 77, No. 4.

L.A. Ruiz-Taylor, et al.; "Monolayers of Derivatized poly(L-lysine)-grafted poly(ethylene glycol) on Metal Oxides as a Class of Biomolecular Interfaces"; PNAS; Jan. 30, 2001; pp. 852-857; vol. 98, No. 3.

Joydeep Lahiri, et al.; "Biospecific Binding of Carbonic Anhydrase to Mixed SAMs Presenting Benzenesulfonamide Ligands: A Model System for Studying Lateral Steric Effects"; Langmuir; 1999; pp. 7186-7198; vol. 15; American Chemical Society.

Notice of Rejection issued in corresponding Japanese Patent Application No. 2008-306521 on Jan. 24, 2012.

* cited by examiner

METHOD OF PRODUCING SUBSTANCE IMMOBILIZING CARRIER

CLAIM OF PRIORITY

The present application claims priority from Japanese patent application JP 2007-315126 filed on Dec. 5, 2007, the content of which is hereby incorporated by reference into this application.

BACKGROUND OF THE INVENTION

1. Field of the Invention

The present invention relates to a method of producing a carrier on which a substance, a biological material such as a protein in particular, can be immobilized stably while retaining its activity.

2. Background Art

The technology of immobilizing biomolecules is used in various applications such as biochips, biosensors, affinity carriers, µTAS, cell culture substrates, etc, and numerous variations thereof are known. One that is drawing particular attention is the method of immobilizing biomolecules through a hydrophilic spacer such as polyethyleneglycol (PEG). A hydrophilic spacer has several excellent effects, which include a reduced rate of deactivation of the biomolecule due to the immobilization, improvement in the mobility of the immobilized biomolecules, suppression of nonspecific adsorption of non-target molecules, and promotion of interactions between biomolecules. However, the hydroxyl groups originally present in PEG have low reactivity and it is therefore generally difficult to form covalent bonds between the PEG and the support surface, or to bind the biomolecule to the free ends of the PEG under physiological conditions. For these reasons, usually, a PEG derivative that has a functional group that is more reactive than the hydroxyl group is used as the hydrophilic spacer.

For example, in JP Patent Publication (Kokai) No. 07-59567A (1995) and Analytical Chemistry, 77, 1096-1105 (2005), PEG derivatives having amino groups at both ends are used as the hydrophilic spacer. In Specification of U.S. Pat. No. 6,033,784, a PEG derivative with a quinone component at one end and an electrophilic functional group at the other end is used as the hydrophilic spacer. A PEG derivative with biotin at one end and an active ester at the other end is used in Proceedings of the National Academy of Sciences, 98, 852-857 (2001). In Langmuir, 15, 7186-7198 (1999), a PEG derivative having a carboxyl group at one end and an alkane thiol at the other end is used. All these documents in the public domain claim that hydrophilic spacers give many excellent effects such as maintenance of the activity of the immobilized biomolecules, improvement of conformational mobility of the immobilized biomolecules, and suppression of nonspecific adsorption of non-target molecules.

SUMMARY OF THE INVENTION

However, these PEG derivatives have never been easy to obtain because of their very high cost, or the need to synthesize them in-house. Because of this, the production cost of substance immobilizing carriers having hydrophilic spacers has been very high.

The present invention has been made against the above background. Its purpose is to provide an inexpensive method of producing a substance immobilizing carrier having a hydrophilic spacer.

The measures described below are adopted in the present invention to solve the problems described above.

In short, the essence of the present invention is to covalently bind an inexpensive hydrophilic compound to the support, and then to introduce a carboxyl group or an active ester into the hydrophilic compound in order to inexpensively produce a substance immobilizing carrier having a hydrophilic spacer. The present invention covers the group of aspects described below.

(1)

A method of producing a substance immobilizing carrier, which comprises: a functional group-introducing step wherein a functional group is introduced on a surface of a support; a hydrophilic compound-binding step wherein a hydrophilic compound having a binding group that can bind with the functional group and a hydroxyl group, is bound to the functional group through bonding between the functional group and the binding group; and a carboxyl group-forming step wherein a carboxyl group is formed through ring-opening half-esterification between a cyclic acid anhydride and a hydroxyl group on the bound hydrophilic compound.

(2)

The method according to (1) wherein the ring-opening half esterification in the carboxyl group-forming step is carried out using 4-dimethylaminopyridine as a catalyst.

(3)

The method according to (1) or (2) wherein the method further comprises an active esterification step in which the carboxyl group formed in the carboxyl group-forming step is converted into an active ester.

(4)

The method according to (3) wherein the active ester is N-hydroxysuccinimide ester.

(5)

The method according to any one of (1) to (4) wherein the support is glass, quartz or silicon.

(6)

The method according to any one of (1) to (5) wherein the functional group introduced on the support is at least one selected from the group consisting of an epoxy group, an aldehyde group, and an amino group.

(7)

The method according to (6), wherein the functional group-introducing step comprises a step in which a silane coupling agent having the functional group is applied to the surface of the support by a sol-gel method.

(8)

The method according to any one of (1) to (7) wherein the hydrophilic compound is at least one selected from the group consisting of ethylene glycol, polyethylene glycol, and a copolymer of ethylene glycol and propylene glycol.

(9)

The method according to any one of (1) to (8) wherein the cyclic acid anhydride is anhydrous succinic acid or anhydrous glutaric acid.

(10)

The method according to any one of (1) to (4) wherein the functional group introduced on the support is an epoxy group, the hydrophilic compound is at least one selected from the group consisting of ethylene glycol, polyethylene glycol, and a copolymer of ethylene glycol and propylene glycol, the cyclic acid anhydride is anhydrous succinic acid or anhydrous glutaric acid, and if the method further has the active esterification step, the active ester is N-hydroxysuccinimide ester.

(11)

The method according to (10) wherein the hydrophilic compound is ethylene glycol or polyethylene glycol, and the cyclic acid anhydride is anhydrous succinic acid.

(12)

The method according to any one of (1) to (4) wherein the functional group introduced on the support is an aldehyde group, the hydrophilic compound is at least one selected from the group consisting of ethylene glycol, polyethylene glycol, and a copolymer of ethylene glycol and propylene glycol, the cyclic acid anhydride is anhydrous succinic acid or anhydrous glutaric acid, and if the method further has the active esterification step, the active ester is N-hydroxysuccinimide ester.

(13)

The method according to (12) wherein the hydrophilic compound is ethylene glycol or polyethylene glycol, and the cyclic acid anhydride is anhydrous succinic acid.

(14)

A substance immobilizing carrier produced according to a method according to any one of (1) to (13).

(15)

A substance immobilizing carrier, which comprises:
a support having a functional group on the surface;
a hydrophilic compound having a binding group that can bind with the functional group and a hydroxyl group; and
a carboxylic acid compound having two carboxylic acid groups, wherein
a bond is formed between the functional group on the support and the binding group of the hydrophilic compound, and
an ester bond is formed between one of the carboxylic acid groups of the carboxylic acid compound and the hydroxyl group of the hydrophilic compound, while the other carboxylic acid group is free or active esterified.

(16)

A substance-immobilized carrier obtained by bringing the substance immobilizing carrier according to (14) or (15) into contact with a substance having a functional group that can bind with a carboxyl group or active ester group in the substance immobilizing carrier to form a covalent bond through a reaction between the carboxyl group or active ester group and the functional group.

(17)

A substance-immobilized carrier obtained by bringing the substance immobilizing carrier according to (14) or (15) into contact with a substance having a functional group that can bind with a carboxyl group or active ester group in the substance immobilizing carrier to form a covalent bond through a reaction between the carboxyl group or active ester group and the functional group, and reacting the carboxyl groups or active ester groups that have not reacted with the functional groups of the substance with an amino group-containing low molecular weight compound.

(18)

The substance-immobilized carrier according to (17), wherein the low molecular weight compound is at least one selected from the group consisting of ethanolamine, trishydroxymethylaminomethane, and diglycolamine.

(19)

The substance-immobilized carrier according to any one of (16) to (18) wherein the substance is a biological material.

(20)

The substance-immobilized carrier according to (19) wherein the biological material is a protein.

A substance immobilizing carrier having a hydrophilic spacer, which used to be expensive, can be produced at low cost in the present invention because there is no need to use an expensive PEG derivative. Besides this, in the present invention, because of the surface density of the carboxyl groups or active esters used for immobilization is suitably low, protein can be immobilized stably while retaining its activity.

Figure 1:
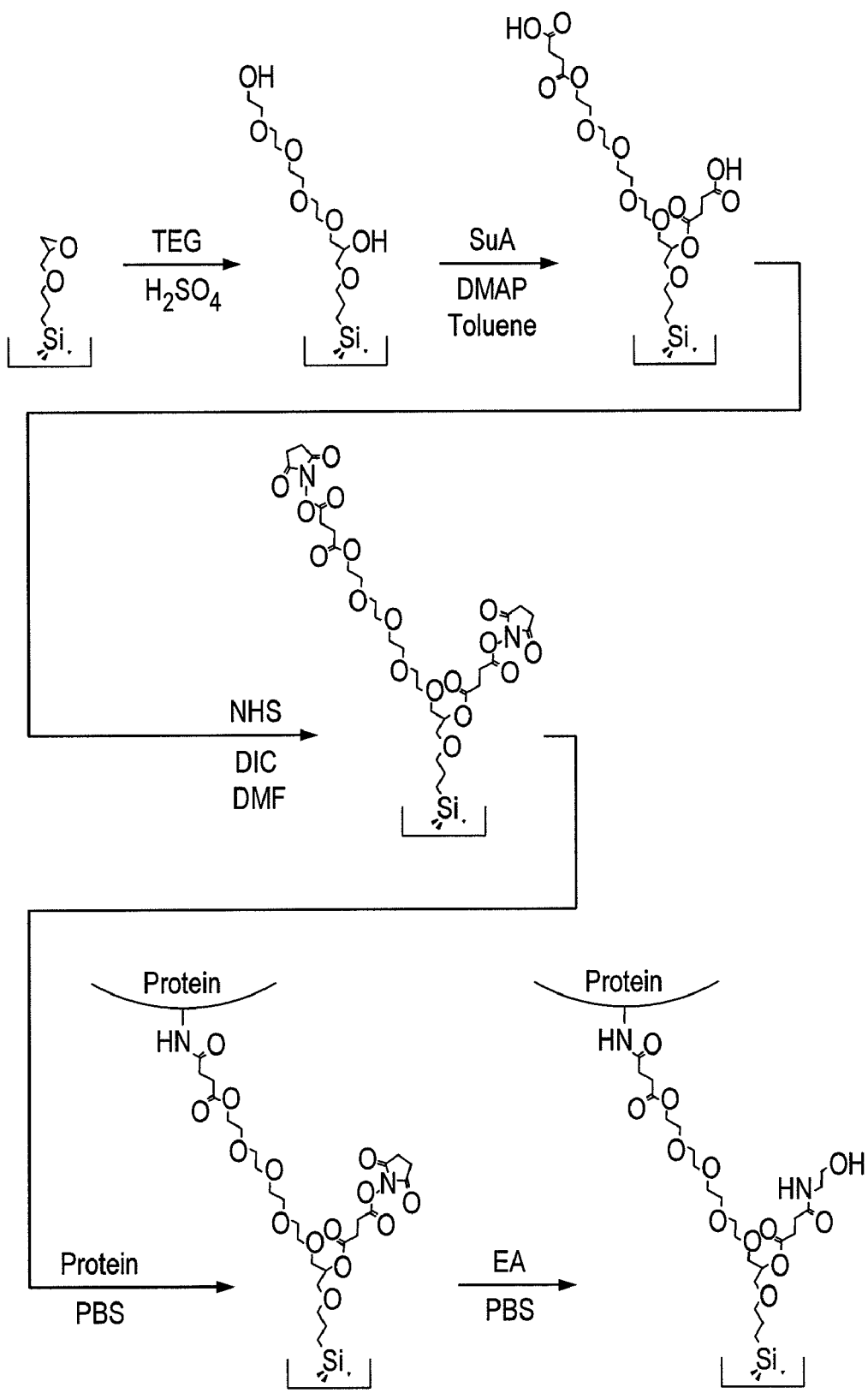
FIG. 1 is one embodiment of the present invention, which has a step of introducing epoxy groups on a glass surface.

DETAILED DESCRIPTION OF THE PREFERRED EMBODIMENTS (Functional Group-introducing Step)

In the present invention, the "functional group introducing step" is a step in which a functional group is introduced on a surface of a support.

There is no particular restriction on the support in the present invention as long as it can provide a surface that is stable against water. Specific examples of materials of the support include inorganic materials such as metals, metal oxides, glass, quartz, silicon, and ceramics; synthetic polymers such as elastomers, plastics, polyester resin, polyethylene resin, polypropylene resin, ABS resin, nylon, acrylic resin, fluorine resin, polycarbonate resin, polyurethane resin, methylpentene resin, phenol resin, melamine resin, epoxy resin, and vinyl chloride resin; and natural polymers such as chitin, chitosan, and cellulose. There is no restriction on the shape of the support, and examples thereof include flat shapes, such flat plate, flat membrane, film, and porous membrane; or three-dimensional shapes, such as a cylinder, stamp, multi-well plate, micropassages, and microparticles. Considering the industrial applicability of the present invention, supports made of glass, quartz, or silicon are particularly preferable.

There are no particular restrictions on the functional group that is introduced on the surface of the support as long as it can covalently bond with the binding group of the hydrophilic compound discussed later. However, when the support is glass, quartz, or silicon, it is preferable for the functional group to be an epoxy group, aldehyde group or amino group, which can be easily introduced using a general-purpose silane coupling agent. Apart from these, it is possible to use N-hydroxysuccinimide group, hydroxyl group, isocyanate group, maleimide group, thiol group, carboxyl group, and carbodiimide group as the functional group, but it is not limited to these examples.

Examples of general-purpose silane coupling agents that can be used in the present invention include silane coupling agents having an epoxy group, aldehyde group or amino group.

A compound represented by the General Formula (I) given below can be used, for instance, as the silane coupling agent having an epoxy group,

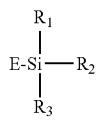

wherein $R_1$, $R_2$, and $R_3$ are independently methyl, methoxy, or ethoxy groups, provided that at least one of $R_1$, $R_2$, and $R_3$ is a methoxy or ethoxy group, and E is a group having an epoxy group, which may be 3-glycidoxypropyl group or 2-(3,4-epoxycyclohexyl)ethyl group. Specific examples include 3-glycidoxypropyl-trimethoxysilane, 3-glycidoxypropyl-triethoxysilane, 3-glycidoxypropyl-methyldimethoxysilane, 3-glycidoxypropyl-methyldiethoxysilane, 3-glycidoxypropyl-dimethylethoxysilane, 2-(3,4-epoxycyclohexyl)ethyltrimethoxysilane, and 2-(3,4-epoxycyclohexyl)ethyltriethoxysilane.

In short, the epoxy group introduced in the functional group-introducing step has the following structure:

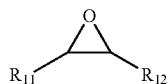

wherein one of $R_{11}$ and $R_{12}$ is a linking group that links the support to the epoxy ring, for example:

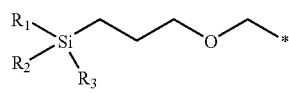

wherein the * represents bonding with the epoxy group, and $R_1$, $R_2$, and $R_3$ are as defined above, and the other is hydrogen or other substituting group, hydrogen being preferable; or $R_1$ and $R_{12}$ together form a ring linked to the support through a linking group, for example:

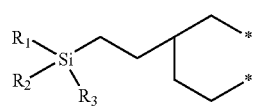

wherein the *s represent bonding to epoxy groups, and $R_1$, $R_2$, and $R_3$ are as defined above.

A compound represented by the General Formula (II) given below can be used, for instance, as the silane coupling agent having an amino group.

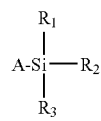

wherein $R_1$, $R_2$, and $R_3$ are as defined above, and A is a group having an amino group, such as 3-aminopropyl group or N-(2-aminoethyl)-3-aminopropyl group). Specific examples include N-(2-aminoethyl)-3-aminopropyltrimethoxysilane, N-(2-aminoethyl)-3-aminopropylmethyldimethoxysilane, N-(2-aminoethyl)-3-aminopropyltriethoxysilane, 3-aminopropyltrimethoxysilane, 3-aminopropyltriethoxysilane, 3-aminopropylmethyldimethoxysilane, 3-aminopropylmethyldiethoxysilane, and 3-aminopropyldimethylethoxysilane.

In short, the amino group introduced in the functional group-introducing step has the following structure:

wherein $R_{13}$ is the linking group that links the support with the amino group, for example:

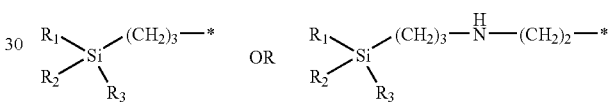

wherein the * represents bonding to the amino group, and $R_1$, $R_2$, and $R_3$ are as defined above.

For introducing aldehyde groups on the surface of the support, the method of acquiring aldehyde groups after introducing epoxy groups or amino groups to the surface of the support can be used, apart from the direct introduction using a silane coupling agent having an aldehyde group.

After introducing epoxy groups to the surface of the support using a general-purpose silane coupling agent or the like, they may be hydrolyzed into diols and then converted into aldehyde groups by oxidative cleavage. In the General Formula (I) given above, when the introduced epoxy group is present in a noncyclic structure, as when the group E is a 3-glycidoxypropyl group, one epoxy group generates one aldehyde group.

[Scheme 1]

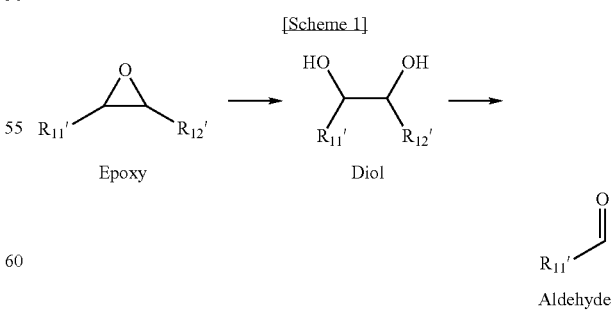

In the Scheme, $R_{11}'$ is a linking group that links together the support and epoxy group, which have been defined above in relation to $R_{11}$ and $R_{12}$, and $R_{12}'$ is a hydrogen or other substituting group defined above in relation to $R_{11}$ and $R_{12}$.

Two aldehyde groups are generated from one epoxy group when the introduced epoxy group is formed in a cyclic structure, as when group E in the above General Formula (I) is 2-(3,4-epoxycyclohexyl)ethyl group.

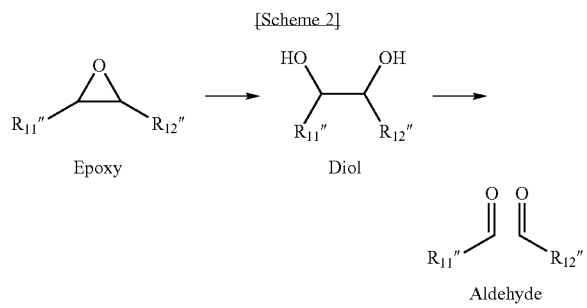

Epoxy    Diol    Aldehyde

[Scheme 2]

In the Scheme, $R_{11}''$ and $R_{12}''$ together form the ring linked to the support via the linking group that has been defined above in relation to $R_{11}$ and $R_{12}$.

An aldehyde group can be introduced after introducing an amino group to the surface of the support using a general-purpose silane coupling agent, or the like, and reacting that amino group with a compound having two aldehyde groups (such as glutaraldehyde). Further, if needed, the carbon-nitrogen double bond (C=N) can be reduced with a reducing agent like sodium borohydride ($NaBH_4$).

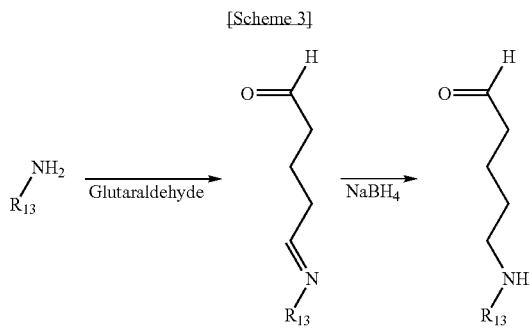

[Scheme 3]

In the Scheme, $R_{13}$ is as defined above.

Examples of methods of applying the general-purpose silane coupling agent to the surface of the support include immersion, sol-gel, vapor phase deposition, spraying, and integral blend methods, but it is not limited to these examples. The most preferable method in the present invention is the sol-gel method. The application of the silane coupling agent by the sol-gel method brings about good results in subsequent steps, such as increase in the amount of a hydrophilic compound bound or the amount of a target substance immobilized. Here, the sol-gel method refers to a method in which a sol obtained by hydrolysis of metal alkoxide is dried into a gel that lacks fluidity, which is then baked to obtain a metal oxide. In the sol-gel method, a spin coating or dip coating method is used for forming a thin film of a sol solution on the surface of a substrate. In the spin coating method, the sol solution is dropped on the substrate, and the substrate is coated with the sol by revolving the substrate at a high speed. In the dip coating method, the substrate is immersed in the sol solution, and the substrate is coated with the sol by pulling the substrate out of the solution at a suitable speed. Typical procedures of application of the silane coupling agent by the sol-gel method are described blow. Firstly, the silane coupling agent and weakly acidic water (pH 3 to 5) are mixed at a suitable ratio, for example, at 1:3 (by mol), and stirred for 15 minutes to 24 hours. This is diluted with isopropyl alcohol (IPA) to prepare a 0.1% to 1.0% sol solution. The surface of the substrate is coated with this using a spin coater. The number of revolutions may be set at 500 to 1500 rpm, and the revolution time at 1 to 10 seconds. After drying for a while, the substrate is heated for 15 to 60 minutes in an oven at 80 to 120° C. Finally, ultrasonic cleansing is carried out in pure water.

(Hydrophilic Compound-binding Step)

In the present invention, the "hydrophilic compound-binding step" is a step wherein a hydrophilic compound having a binding group that can bind with the functional group introduced to the surface of the support through the above-described operation and a hydroxyl group, is bound to the functional group through bonding between the functional group and the binding group.

The hydrophilic compound having the binding group and hydroxyl group functions as the hydrophilic spacer between the support and the substance. Here, hydrophilic spacer means a water-soluble organic chemical structure having at least the function of anchoring the substance to the support through a covalent bond. It is preferable for the hydrophilic compound to have a chain structure for it to function as the hydrophilic spacer, and it is particularly preferable that the hydrophilic compound with the chain structure has a binding group at one end of the chain and a hydroxyl group at the other end. The "binding group" that can bind to the functional group introduced on the surface of the support can be a hydroxyl group or a different functional group from hydroxyl group (such as amino group, epoxy group, aldehyde group, carboxyl group, N-hydroxysuccinimide group, isocyanate group, maleimide group, thiol group, and carbodiimide group), but it is preferable for it to be a hydroxyl group. When the "binding group" is a hydroxyl group, on one molecule of the hydrophilic compound, there will be a hydroxyl group that functions as the binding group and another hydroxyl group that is used for the ring-opening half-esterification reaction with the cyclic acid anhydride, which will be discussed later. In other words, there will be two hydroxyl groups on one molecule. It is preferable for the hydrophilic spacer to show effects like reduced rate of deactivation of the substance due to its immobilization, improvement in the mobility of the immobilized substance, suppression of non-specific adsorption of non-target molecules, and promotion of interactions between substances. There are no particular restrictions on the hydrophilic compound as long as it shows at least one of these effects, but chain-structured hydrophilic compounds with one hydroxyl group at each end are preferable, considering the cost of production. More specifically, at least one compound selected from the group consisting of ethyleneglycol, polyethylene glycol, and a copolymer of ethyleneglycol and propyleneglycol is preferable. There are no particular restrictions on the polyethylene glycol as long as two or more ethyleneglycol molecules are polymerized, and the number average molecular weight is 1000 or more, for instance. But it is preferable if the number average molecular weight is not more than 10000, not more than 4000 being particularly preferable. It is preferable if the copolymer of ethyleneglycol and propyleneglycol is a block copolymer. Among them, block copolymers in which (poly)ethyleneglycol blocks comprising one or more ethyleneglycol units are copolymerized at both ends of (poly)propyleneglycol block(s) comprising one or more propyleneglycol units are preferable. Although there is no specific restriction on the number average molecular weight of the copolymer of ethyleneglycol and propyleneglycol, as long as it is 1000 or more, it is preferable that it is not more than 12000, not more than 4000 being particularly preferable. In the present invention, "propyleneglycol" means 1,2-propanediol.

Hydrophilic Compound-binding Reaction—Embodiment 1

When binding a hydrophilic compound having two hydroxyl groups with the epoxy group introduced on the surface of the support, one hydrophilic compound molecule binds to one epoxy group.

[Scheme 4]

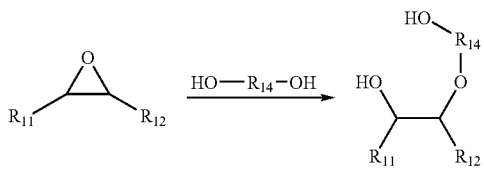

In the Scheme, $R_{11}$ and $R_{12}$ are as defined above, provided that when one of $R_{11}$ and $R_{12}$ is the linking group that links the support with the epoxy ring, and the other is hydrogen, more often, $R_{11}$ is the linking group that links the support with the epoxy ring and $R_{12}$ is hydrogen.

HO—$R_{14}$—OH is a hydrophilic compound having two hydroxyl groups. For example, it represents the above described ethyleneglycol, polyethylene glycol, or copolymer of ethyleneglycol and propyleneglycol. $R_{14}$ represents the structure of the aforementioned ethyleneglycol, polyethylene glycol, or copolymer of ethyleneglycol and propyleneglycol minus the hydroxyl groups at the two ends.

Hydrophilic Compound-binding Reaction—Embodiment 2

When binding a hydrophilic compound having two hydroxyl groups to the aldehyde group introduced on the surface of the support, two hydrophilic compound molecules bind to one aldehyde group.

[Scheme 5]

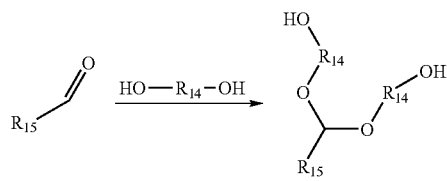

In the Scheme, HO—$R_{14}$—OH and $R_{14}$ are as defined above, and $R_{15}$ stands for a group formed together by $R_{11}'$, $R_{11}''$, and $R_{12}''$ defined above, or

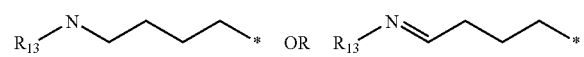

wherein $R_{13}$ is as defined above; the * is the bond with the aldehyde group.

(Carboxyl Group-forming Step)

In the present invention, the carboxyl group forming step is the step where the hydroxyl group (this is the hydroxyl group not used in the reaction in the hydrophilic compound-binding step when the binding group also is a hydroxyl group) on the hydrophilic compound bound in the above described hydrophilic compound-binding step is reacted with a cyclic acid anhydride for ring-opening half-esterification to form a carboxyl group originating from the cyclic acid anhydride.

Considering the cost of production, it is preferable for the cyclic acid anhydride to be anhydrous succinic acid or anhydrous glutaric acid, but it is not limited to these. When using anhydrous succinic acid or anhydrous glutaric acid as the cyclic acid anhydride, the ring-opening half-esterification reaction follows the scheme shown below.

[Scheme 6]

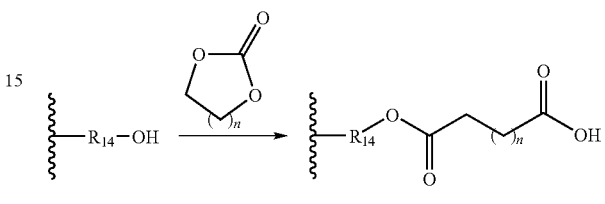

In the Scheme, n represents 1 or 2, $R_{14}$ is as defined above.

When this reaction is applied to the $R_{14}$—OH group that has been bound according to Scheme 4, the hydroxyl group on the carbon to which $R_{11}$ is bound generated in Scheme 4 also undergoes ring-opening half-esterification as a side reaction.

There are no particular restrictions on the catalyst used in the ring-opening half-esterification reaction as long as it promotes the main reaction. Specific examples include triethylamine, isobutylethylamine, pyridine, and 4-dimethylaminopyridine. Triethylamine and 4-dimethylaminopyridine are preferable. 4-dimethylaminopyridine is most preferable, considering the reaction rate and yield (see Example 3).

The ring-opening half-esterification reaction is preferably carried out in an inert organic solvent like toluene whereto the above described catalyst is added.

When using anhydrous succinic acid as the cyclic acid anhydride, and 4-dimethylaminopyridine as the catalyst, it is preferable to set the concentration of the anhydrous succinic acid and the 4-dimethylaminopyridine at 1 to 50 mM each, the reaction temperature at 4 to 100° C., and the reaction time at 2 minutes to 16 hours. Here, the extent of induction of the carboxyl group into the above-described hydrophilic compound can be controlled by regulating the reaction conditions (the concentration of the reagents, reaction temperature, and reaction time). In other words, if the concentration of the reagents and the reaction temperature are set low, or the reaction time is made short, the ultimate surface density of the carboxyl groups or active esters would be low. On the other hand, if they were set high or long, the surface density of the carboxyl groups or the active esters would be high. It is desirable to suitably regulate the surface density of the carboxyl groups or the active esters according to the type of substance to be immobilized. For instance, for immobilizing DNA or peptide, it is better to keep the surface density of the carboxyl groups or active esters as high as possible, and to keep it rather low for immobilizing proteins.

(Active Esterification Step)

In the present invention, the "active esterification step" is the step wherein the carboxyl groups formed in the above described carboxyl group-forming step are converted into the active esters. Conversion of the carboxyl groups into active esters is not essential. However, because active esters have a higher reactivity compared to the carboxyl groups, it is preferable to have the active esterification step when the target substance is to be immobilized rapidly on the carrier.

The active ester plays the role of binding the hydrophilic compound with the substance to be immobilized, through covalent bonding. Here, active ester means the chemical structure R—C(=O)—X. Here, X represents a leaving group like halogen, N-hydroxysuccinimide group or derivatives thereof, 1-hydroxybenzotriazole group or derivatives thereof, pentafluorophenyl group, and para-nitrophenyl group, but is not limited to these groups. N-hydroxysuccinimide ester is preferable as the active ester considering the reactivity, safety, and production cost. The conversion of the above described carboxyl group into N-hydroxysuccinimide ester is achieved by the simultaneous reactions of N-hydroxysuccinimide and carbodiimide with the carboxyl group. Here, carbodiimide means an organic compound having the chemical structure of —N=C=N—, and examples thereof include dicyclohexylcarbodiimide, diisopropylcarbodiimide, and 1-ethyl-3-(3-dimethylaminopropyl)carbodiimide hydrochloride, but it is not limited to these. It is preferable to set the concentration of the N-hydroxysuccinimide and carbodiimide at 1 to 100 mM, the reaction temperature at 4 to 100° C., and the reaction time at 2 minutes to 16 hours. N,N'-dimethylformamide (DMF), toluene, etc., can be used as a reaction solvent.

(Substance Immobilizing Carrier)

The present invention is also related to a substance immobilizing carrier produced by the method comprising the above-described steps, and having the carboxyl groups or active ester groups positioned on the support.

Typical structures of the substance immobilizing carrier of the present invention are given below.

Structure of Substance Immobilizing Carrier—Embodiment 1

The substance immobilizing carrier obtained in the method of production of the present invention has a structure wherein the chemical structure shown below is formed on the support when the functional group introduced on the support is an epoxy group, the hydrophilic compound is at least one selected from the group consisting of ethyleneglycol, polyethylene glycol, and a copolymer of ethyleneglycol and propyleneglycol, the cyclic acid anhydride is anhydrous succinic acid or anhydrous glutaric acid, and the method further has an active esterification step, and the active ester is N-hydroxysuccinimide ester,

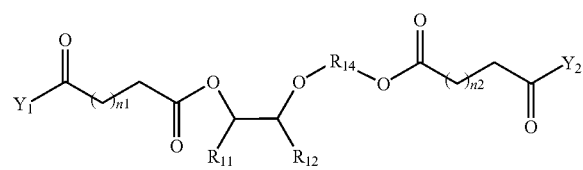

wherein $Y_1$ and $Y_2$ are, independently, —OH or N-hydroxysuccinimide group, n1 and n2 are, independently, integers 1 or 2, and $R_{11}$, $R_{12}$, and $R_{14}$ are as defined above.

Structure of Substance Immobilization Carrier—Embodiment 2

The substance immobilizing carrier obtained in the method of production of the present invention has a structure wherein the chemical structure shown below is formed on the support when the functional group introduced on the support is an aldehyde group, the hydrophilic compound is at least one selected from the group consisting of ethyleneglycol, polyethylene glycol, and a copolymer of ethyleneglycol and propyleneglycol, the cyclic acid anhydride is anhydrous succinic acid or anhydrous glutaric acid, and the method further has an active esterification step, and the active ester is N-hydroxysuccinimide ester,

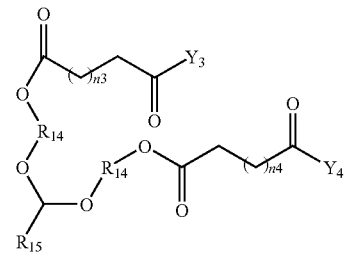

wherein $Y_3$ and $Y_4$ are, independently, —OH or N-hydroxysuccinimide group, n3 and n4 are, independently, integers 1 or 2, and $R_{14}$ and $R_{15}$ are as defined above.

In Embodiment 2, the structure has two branches as shown above, as two molecules of the hydrophilic compound are bound to one aldehyde group. Because of this structure, when the protein is immobilized, the activity per molecule of the immobilized protein is retained remarkably well (see FIG. 8). The substance immobilizing carrier having this type of structure has not been produced until now.

(Immobilization of Substance)

There is no particular restriction on the substance immobilized in the present invention as long as it has a functional group capable of forming a covalent bond by reacting with a carboxyl group or an active ester. A typical example of such functional groups includes amino group, but other examples include thiol group, carboxyl group, hydroxyl group, alkoxide, secondary amine, tertiary amine, azide group, cyano group, Grignard reagent, organic lithium compounds, and carbanion. A biological material is preferable as the substance to be immobilized. Examples of biological materials include DNA, RNA, peptides, hormones, enzymes, antigens, antibodies, cytokines, sugar chains, lipids, coenzymes, enzyme inhibitors, cells, and proteins having other functions. Further, low molecular weight compounds, and high molecular weight compounds with affinity for these types of biological materials are also included in the category of biological materials.

The present invention works particularly well when the biological material is a protein. In other words, the lowering of activity of the protein as a result of the immobilization is relatively well mitigated in the present invention. It is believed that this is because the surface density of the carboxyl group or active ester is made suitably low because of the adoption of the multi-step production method. Furthermore, even when the biological material to be immobilized does not have functional groups such as amino groups, which can form bonds through reaction with the carboxyl group or active ester, it can be immobilized by artificially introducing amino groups, etc., into the biological material.

The reaction between the substance to be immobilized and the active ester positioned on the support can be carried out, for instance, as follows. Firstly, an aqueous solution containing 0.1 to 1 mg/ml of the substance to be immobilized is prepared using buffer not containing amino groups, such as citrate buffer (pH 3.0 to 6.2), acetate buffer (pH 3.6 to 5.6), phosphate buffer saline (PBS, pH 5.8 to 8.0), or carbonate-bicarbonate buffer (pH 9.2 to 10.6). When the substance to be immobilized is a protein, it is preferable to optimize the buffer or pH to give the maximum amount immobilized. The buffer can contain a stabilizing agent such as glycerol or polyethyleneglycol, salt (NaCl), a surfactant, etc. These do not inhibit the reaction between the active ester and the substance to be immobilized. When the aqueous solution is brought into contact with surface having the active ester, the functional group, such as amino group, present in the substance to be immobilized reacts with the active ester, forming an amide bond. As a result, the target substance is immobilized on the surface through covalent bonding. Here, the reaction temperature may be set at 4 to 37° C., and contact time at 2 minutes to 16 hours. After immobilizing the target substance, it is preferable to wash the carrier with a suitable washing solution. It is preferable for this washing solution to be buffer containing about 0.5 M salt (NaCl) and about 0.1% nonionic surfactant. This can remove the target substance immobilized only through physical adsorption without covalent bonding.

After immobilizing the target substance on the surface of the carrier (preferably, after further washing the substance-immobilized carrier), it is preferable to bind the unreacted carboxyl groups or active esters with a low molecular weight compound having an amino group, to convert the carboxyl groups or active esters into less reactive functional groups. This prevents non-target molecules from getting inadvertently immobilized on the surface of the carrier. The need for this step is particularly high when the functional group at the end of the substance immobilizing carrier is an active ester.

In this description, the operation of reacting a low molecular weight compound having an amino group with the active ester group is sometimes called "inactivation". However, it is preferable that the surface of the carrier, after the reaction of the low molecular weight compound with the carboxyl groups or active esters, is hydrophilic. This is because hydrophilic surfaces generally have the effect of suppressing non-specific adsorption of biological materials. For this purpose, it is preferable to use a low molecular weight compound having hydrophilic groups in addition to the amino group as the amino group-containing low molecular weight compound. Nonexclusive examples of such low molecular weight compounds include ethanolamine, trishydroxymethylaminomethane, and diglycolamine (IUPAC name: 2-(2-aminoethoxy)ethanol). Among them, diglycolamine is particularly excellent in the effect of suppressing nonspecific adsorption of biological materials. This low molecular weight compound is dissolved in a buffer such as PBS to make a 10 to 50 mM solution and then brought into contact with the carrier whereon the desired substance has been immobilized. The reaction temperature may be set at 4 to 37° C. and the reaction time at 2 minutes to 16 hours.

(Control of the Production Process of the Substance Immobilizing Carrier)

It is convenient to use measurement of water contact angle, and x-ray photoelectron spectroscopic measurement (XPS/ESCA) for controlling the production process of the substance immobilizing carrier according to the present invention. Changes in surface properties can be determined rapidly and easily by measuring the water contact angle. For example, the binding of a hydroxyl group-containing hydrophilic compound to the surface of the support in most cases brings about a lowering of the water contact angle. The reaction with the cyclic acid anhydride or conversion of the carboxyl group into active ester increases the water contact angle, although these depend on the molecular weight of the hydrophilic compound. XPS/ESCA is a technique of analyzing the constituent elements of the sample and their binding status through measurement of the kinetic energy of photoelectrons generated when the sample surface is irradiated with x-rays. At the time of the measurement, the range of binding energy to be scanned is chosen according to the elements that constitute the support and the hydrophilic compound.

For example, when the support is glass, quartz or silicon, and the hydrophilic compound is ethyleneglycol, polyethylene glycol, or copolymer of ethyleneglycol and propyleneglycol, the measurement is made for a total of four elements, i.e., carbon (C1s), oxygen (O1s), nitrogen (N1s), and silicon (Si2p), and the range of binding energy characteristic of each element is scanned. The number of photoelectrons arising from each element divided by the number of photoelectrons of all the elements measured is defined as the "elemental concentration (%)" of that element. For example, the concentration of carbon can be expressed by (number of photoelectrons originating from C1s)/{(number of photoelectrons originating from C1s)+(number of photoelectrons originating from O1s)+(number of photoelectrons originating from N1s)+(number of photoelectrons originating from Si2p)}. The C1s peak can be separated into three peaks with maximum values around 285 eV, 287 eV, and 289 eV, depending on the status of binding of the carbon atom, and these peaks correspond to C—C/C—H, C—O, and C(=O)—O. When the cyclic acid anhydride reacts, ester bonds and carboxyl groups are newly formed, which enhances the peak around 289 eV. The nitrogen concentration increases in most cases when the carboxyl group is converted into active ester. This is because many types of active esters have nitrogen atoms within their molecules. By following these changes it is verified whether the series of chemical reactions of the present invention have advanced properly or not.

The three parameters described below must be set for evaluating the substance immobilizing carrier. The first parameter is the activity of the immobilized protein, the second is the speed of immobilization of the protein and the amount immobilized, and the third is the amount of nonspecific adsorption of non-target molecules.

The reason for evaluating the first parameter is that it is desirable to retain, to the extent possible, the activity of the protein immobilized on the surface. For example, when an enzyme is immobilized on the substance immobilizing carrier, it is desirable that the catalytic activity of the enzyme is retained. The activity of the immobilized enzyme can be evaluated easily by measuring the amount of substrate reacted in terms of absorbance or intensity of fluorescence. Here, it is appropriate to assume that the higher the absorbance or fluorescence intensity, the higher is the retention of the activity of the immobilized enzyme. Horseradish peroxidase (HRP) is recommended as a model enzyme for reasons of low cost and ease in handling. But alkali phosphatase, β-galactosidase, etc., may also be used. One thing to be kept in mind here is that the enzymatic activity measured by this method is not only from the enzyme immobilized through covalent bonding, as some of it comes from the physically adsorbed enzyme. If the activity of the enzyme immobilized by covalent bonding alone is to be evaluated, the activity of the enzyme physically adsorbed on the immobilizing carrier where the active ester has been inactivated using ethanolamine, etc., needs to be measured separately as a control.

The reason for evaluating the second parameter is that it is preferable to immobilize as much protein as possible in as short a time as possible. The use of enzyme-linked immunosorbent assay (ELISA) is simplest way of evaluating the second parameter, i.e., speed of immobilization of the substance and the amount immobilized. Firstly, a suitable protein is immobilized on the substance immobilizing carrier. It is then linked to an enzyme-labeled antibody that specifically binds to the protein. After that, the substrate solution is added to the surface of the substance immobilizing carrier and the amount of substrate that reacts with the enzyme used for labeling the antibody is evaluated through measurement of absorbance or fluorescence intensity. Here, it is assumed that the higher the absorbance or fluorescence intensity, the greater is the amount of protein immobilized on the carrier. Bovine serum albumin (BSA) is suitable for use as a model protein because it is inexpensive and easy to handle. Enzyme-labeled antibodies that specifically bind to BSA are relatively inexpensive to obtain. It is particularly simple and economical if the enzyme used for evaluating the first parameter and the one used for labeling the antibody are the same because then only one type of substrate need to be prepared.

It is preferable to use HRP-labeled antibody for evaluating the second parameter in cases where HRP had been used for evaluating the first parameter. One thing to be kept in mind here is that the amount of immobilized BSA evaluated by this method is not just the BSA immobilized through covalent bonding, as some of it is BSA that is physically adsorbed. Therefore, if the amount of the BSA immobilized by covalent bonding alone is to be evaluated, the amount of BSA physically adsorbed on the substance immobilizing carrier, where the active ester has been inactivated using ethanolamine, etc., needs to be measured separately as a control.

The amount of BSA physically adsorbed on the substance immobilizing carrier where the active esters have been inactivated with ethanolamine, and the like is nothing but the amount of nonspecific adsorption of non-target molecules (the third parameter). The reason for evaluating this amount is that it is preferable to suppress the nonspecific adsorption of non-target molecules, once the target substance has been immobilized on carrier. The evaluation procedure involves immersion of the surface, the active esters whereon have been inactivated using ethanolamine, in a BSA-containing buffer, followed by binding HRP-labeled anti-BSA antibody to the BSA physically adsorbed on the surface. The substrate solution is then added to the surface of the substance immobilizing carrier, and the amount of substrate that reacts with the HRP used to label the antibody is evaluated in terms of absorbance or fluorescence intensity. Here, it is assumed that the lower the absorbance or fluorescence intensity, the higher is the suppressive effect on nonspecific adsorption of substances.

The present invention is explained below through specific examples.

EXAMPLE 1

The example shown in FIG. 1 comprises a step of introducing epoxy groups on a glass surface, a step of covalent bonding of tetraethyleneglycol (TEG) to the epoxy group, a step of forming a carboxyl group by reacting anhydrous succinic acid with the hydroxyl groups present at the free ends of the TEG, a step of converting the carboxyl groups into active esters, a step of reacting a protein with an active ester, and a step of inactivating the unreacted active ester using ethanolamine. The specific procedures are described below.

39 g of toluene (Junsei Chemical), 450 μl of 3-glycidoxypropyltrimethoxysilane (TSL8350, GE Toshiba Silicone), 900 μl of triethylamine (Wako Pure Chemical Industries) were mixed, and a 10 cm square UV-cleansed glass substrate (NA35, NH Technoglass) was immersed in it and shaken mildly for 20 hours at room temperature. After that, the substrate was washed with ethanol and water and nitrogen blow-dried. Epoxy groups were introduced on the glass surface by this operation. Next, the glass substrate was immersed in TEG (Kanto Chemical) containing a catalytic amount of concentrated sulfuric acid and heated for 1 hour at 80° C. After this reaction, the substrate was washed well with water and nitrogen blow-dried. By this operation, the TEG reacted with the epoxy groups and formed covalent bonds. Next, 100 mg of anhydrous succinic acid (SuA, Kanto Chemical) and 120 mg of 4-dimethylaminopyridine (DMAP, Wako Pure Chemical Industries) were dissolved in 43 g of toluene, the above substrate immersed in it, and heated for 1 hour at 80° C. After that, the substrate was washed with ethanol and water, and nitrogen blow-dried. The ring-opening half-esterification reaction advanced in this step and carboxyl groups were introduced on the free ends of the TEG. Next, 290 mg of N-hydroxysuccinimide (NHS, Wako Pure Chemical Industries) and 390 μl of N,N'-diisopropylcarbodiimide (DIC, Wako Pure Chemical Industries) were dissolved in 47 g of N,N'-dimethylformamide (DMF, Kanto Chemical), and the substrate was immersed in it and heated for 1 hour at 80° C. After that, the substrate was washed with ethanol and water, and nitrogen blow-dried. N-hydroxysuccinimide (NHS) groups were introduced at the free ends of the TEG by this operation. Lastly, the substrate was cut into pieces of size 25 mm×10 mm.

In the substance immobilizing carrier prepared by the procedure described above, TEG functions as the hydrophilic spacer. Substance immobilizing carriers having ethyleneglycol (EG, Aldrich), PEG 600 (Kanto Chemical), PEG 1000 (Kanto Chemical), PEG 2000 (Kanto Chemical), or PEG 4000 (Kanto Chemical) as the hydrophilic spacer in place of TEG were also prepared in a similar manner. The water contact angle of the surface of these carriers changed as shown in Table 1.

TABLE 1

| Terminal functional group | Spacer | | | | | |
|---|---|---|---|---|---|---|
| | EG | TEG | PEG600 | PEG1000 | PEG2000 | PEG4000 |
| Epoxy group | 51.8 | 52.2 | 52.3 | 52.4 | 51.9 | 52.4 |
| Hydroxyl group | 24.2 | 29.3 | 29.6 | 29.8 | 28.8 | 29.0 |
| Carboxyl group | 33.6 | 34.8 | 30.5 | 30.4 | 29.3 | 29.7 |
| NHS group | 40.3 | 38.5 | 33.4 | 31.0 | 30.1 | 29.3 |

The elemental concentration of carbon (C1s), oxygen (O1s), nitrogen (N1s), and silicon (Si2p) changed as shown in Table 2 when TEG or PEG400 was used as the hydrophilic spacer.

TABLE 2

| Spacer | Terminal functional group | C1s, % | | | O1s, % | N1s, % | Si2p, % |
|---|---|---|---|---|---|---|---|
| | | C—C, C—H | C—O | O=C—O | | | |
| TEG | Hydroxyl group | 12.8 | 27.3 | 1.6 | 41.7 | 0.3 | 16.2 |
| | Carboxyl group | 11.4 | 29.3 | 5.0 | 41.2 | 0.3 | 12.8 |
| | NHS group | 12.4 | 27.7 | 5.8 | 40.0 | 1.1 | 13.0 |

TABLE 2-continued

| Spacer | Terminal functional group | C1s, % | | | | O1s, % | N1s, % | Si2p, % |
| --- | --- | --- | --- | --- | --- | --- | --- | --- |
| | | C—C, C—H | C—O | O═C—O | | | | |
| PEG4000 | Hydroxyl group | 9.2 | 38.5 | 1.5 | | 38.8 | 0.3 | 11.6 |
| | Carboxyl group | 9.6 | 35.5 | 3.5 | | 39.6 | 0.4 | 11.4 |
| | NHS group | 9.8 | 37.7 | 3.8 | | 37.6 | 0.8 | 10.4 |

These results show that the series of chemical reactions of the present invention had advanced properly.

HRP (Wako Pure Chemical Industries) was immobilized on the substance immobilizing carriers (25 mm×10 mm) prepared above, and the enzymatic activity was measured. The specific procedure used is described below.

1 mg/ml HRP solution (in a 1:1 mixture of PBS and glycerol) and the substance immobilizing carrier were brought into contact, and incubated for 10 minutes at room temperature. This allowed the reaction between the active esters on the surface of the carrier and HRP to occur, and the HRP to get immobilized on the surface of the carrier. Next, the surface of the carrier was washed three times with PBS containing 0.05% Tween 20 (hereinafter referred to as "washing buffer"), the surface was then brought into contact with 50 mM ethanolamine (EA), and incubated for 10 minutes at room temperature. By doing this, the unreacted active esters were almost completely inactivated. After washing three times with the washing buffer, 200 µl of a PBS solution of 5 mM SAT-3 (Dojin Chemical), which is a chromogenic substrate for HRP, and 0.5 mM aqueous hydrogen peroxide (Kanto Chemical) (hereinafter referred to as "substrate solution") was dropped on the surface of the carrier, and the carrier incubated at room temperature for 10 minutes. Immediately after that, 100 µl of the substrate solution was sampled and transferred to a 96-well multi-well plate. 100 µl of 1M sulfuric acid was added to this and the absorbance at 474 nm measured with a plate reader (SpectraMax M2$^e$, Molecular Devices).

To subtract the contribution of the physically adsorbed HRP fraction from the measured value, the surface of a carrier where the active esters were inactivated by ethanolamine was also evaluated in a similar way. First, the substance immobilizing carrier was brought into contact with 50 mM ethanolamine and incubated at room temperature for 10 minutes. This almost completely inactivated the active esters on the surface of the carrier. Next, the surface of the carrier was washed three times with the washing buffer, brought into contact with 1 mg/ml HRP solution, and incubated for 10 minutes at room temperature. By doing this, the HRP got physically adsorbed on the carrier surface without being immobilized. After washing the carrier three times with the washing buffer, 200 µl of the substrate solution was dropped on the carrier surface, and it was incubated for 10 minutes at room temperature. Immediately after that, 100 µl of the substrate solution was sampled, and transferred to a 96-well multi-well plate. 100 µl of 1M sulfuric acid was added to this and the absorbance at 474 nm measured with the plate reader.

Figure 2:
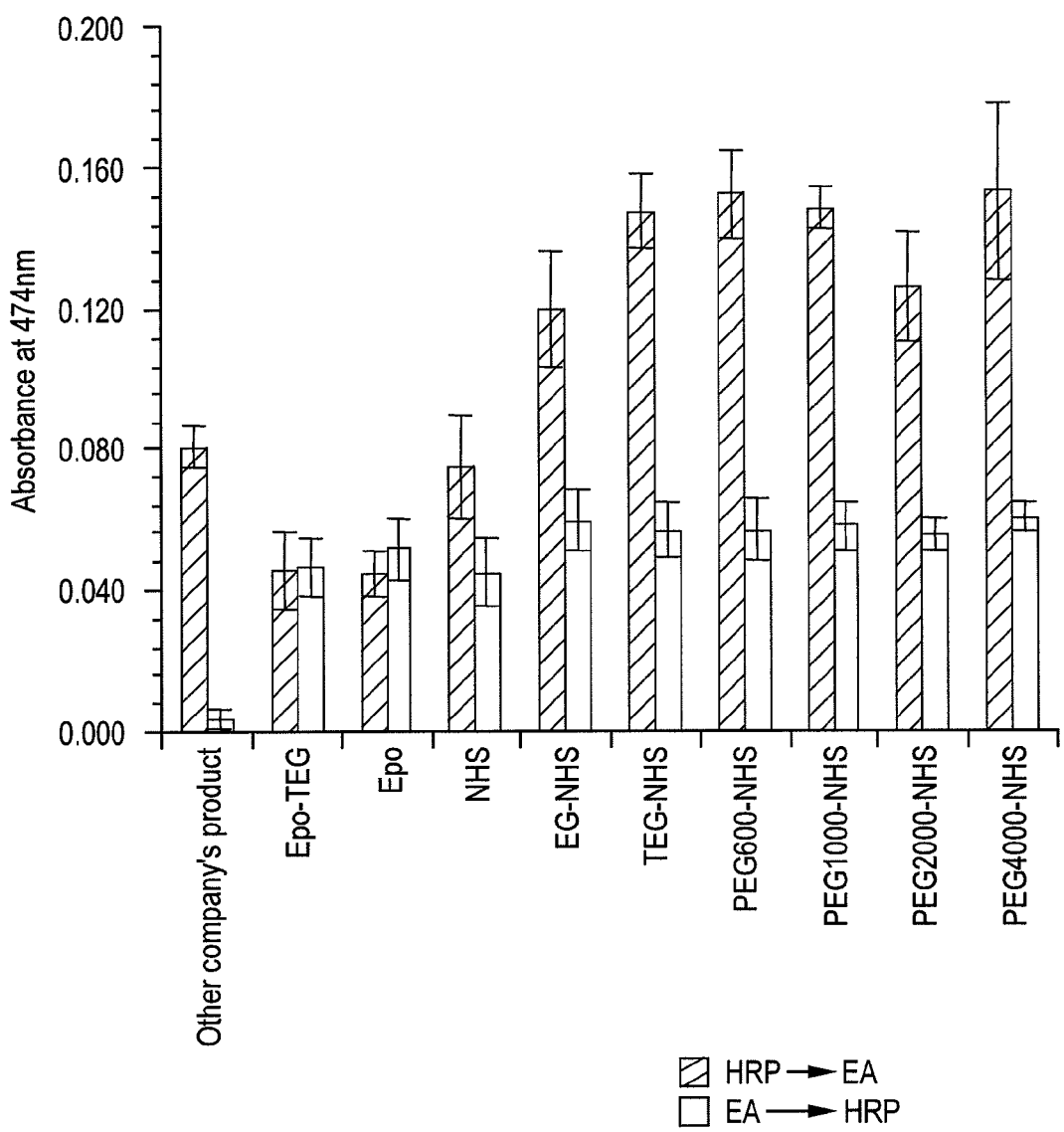
FIG. 2 is the result of measurement of activity of immobilized HRP in Example 1 (including the Comparative Examples).

In the above procedure, the surface of the carrier incubated in the order HRP→EA has both HRP immobilized through covalent bonding as well as physically adsorbed HRP. On the other hand, the surface of the carrier incubated in the order EA→HRP has almost no HRP immobilized through covalent bonding and some amount of HRP adsorbed physically. Therefore, the amount obtained by subtracting the EA→HRP value from the HRP→EA value can be taken as the activity of HRP immobilized through covalent bonding. FIG. 2 gives the results of measurements when the hydrophilic spacer was EG, TEG, PEG 600, PEG 1000, PEG 2000, and PEG 4000. The sample names respectively assigned for these were "EG-NHS", "TEG-NHS", "PEG 600-NHS", "PEG 1000-NHS", "PEG 2000-NHS", and "PEG 4000-NHS". In all samples, HRP→EA showed higher enzymatic activity than EA→HRP. This meant that HRP immobilized on the surface of the carrier through covalent bonds were maintaining their activity to some extent.

Next, BSA (Wako Pure Chemical Industries) was immobilized on substance immobilizing carriers (25 mm×10 mm) and the amount immobilized was evaluated by ELISA. The specific procedure used is described below.

1 mg/ml BSA solution (in a 1:1 mixture of PBS and glycerol) was brought into contact with the substance immobilizing carrier and incubated for 10 minutes at room temperature. This allowed the reaction between the active esters on the surface of the carrier and BSA to occur, and the BSA to get immobilized on the surface of the carrier. The surface of the carrier was then washed three times with the washing buffer, brought into contact with 50 mM ethanolamine (EA), and incubated for 10 minutes at room temperature. By doing this, the unreacted active esters were almost completely inactivated. After washing three times with the washing buffer, the surface of the carrier was brought into contact with HRP-labeled anti-BSA antibody (AbCam) solution in PBS (5 µg/ml), and incubated for 30 minutes at room temperature. By doing this, the HRP-labeled antibodies got bound to the BSA immobilized or physically adsorbed on the surface of the carrier. The surface of the carrier was then washed three times with the washing buffer, 200 µl of the substrate solution was dropped on the surface, and the carrier was incubated for 10 minutes at room temperature. Immediately after that, 100 µl of the substrate solution was sampled and transferred to a 96-well multi-well plate. 100 µl of 1M sulfuric acid was added to this and the absorbance at 474 nm measured with the plate reader.

To subtract the contribution by the BSA fraction physically adsorbed on the carrier, from the measured value, the surface of a carrier where the active esters were inactivated by ethanolamine was also evaluated in a similar way. First, the substance immobilizing carrier was brought into contact with 50 mM ethanolamine (EA) and incubated for 10 minutes at room temperature. This almost completely inactivated the active esters on the surface of the carrier. Next, the surface of the carrier was washed three times with the washing buffer, brought into contact with 1 mg/ml BSA solution, and incubated for 10 minutes at room temperature. By doing this, the BSA got physically adsorbed without being immobilized on the surface of the carrier. After washing three times with the washing buffer, the surface of the carrier was brought into contact with HRP-labeled anti-BSA antibody solution in PBS (5 µg/ml), and incubated for 30 minutes at room temperature. By doing this, the HRP-labeled antibody got bound to the BSA physically adsorbed on the carrier surface. After washing the surface three times with the washing buffer, 200 µl of the substrate solution was dropped on the surface of the carrier, and it was incubated for 10 minutes at room temperature. Immediately after that, 100 µl of the substrate solution was sampled, and transferred to a 96-well multi-well plate. 100 µl of 1M sulfuric acid was added to this and the absorbance at 474 nm was measured with the plate reader.

Figure 3:
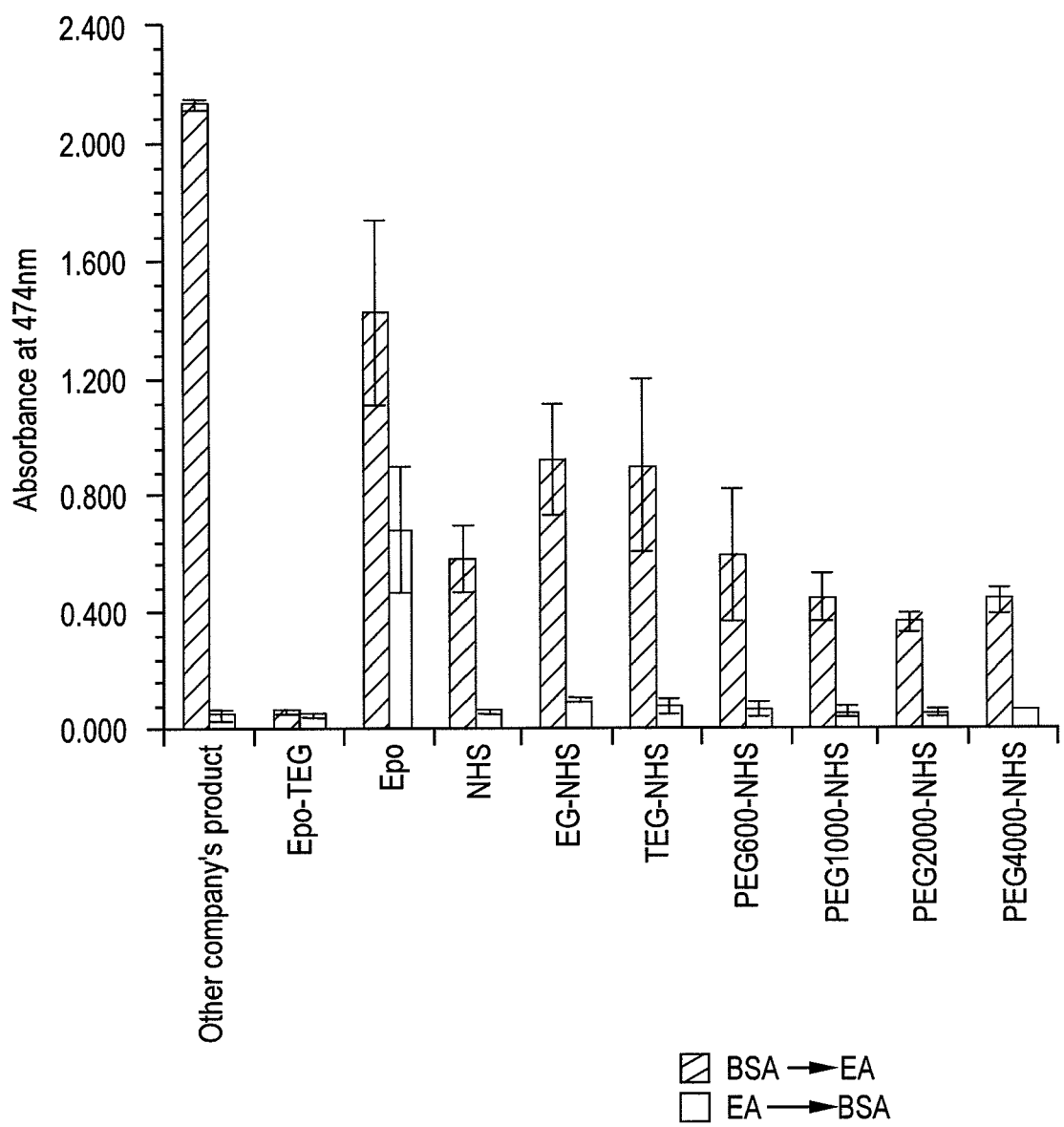
FIG. 3 is the result of measurement of the amount of immobilized BSA in Example 1 (including the Comparative Examples).

In the aforesaid procedure, the surface of the carrier incubated in the order BSA→EA has both BSA immobilized through covalent bonding as well as physically adsorbed BSA. On the other hand, the surface of the carrier incubated in the order EA→BSA has almost no BSA immobilized through covalent bonding, and some amount of BSA adsorbed physically. Therefore, the amount obtained by subtracting the EA→BSA value from the BSA→EA value reflects the amount of BSA immobilized through covalent bonding. FIG. 3 gives the results of measurements when the hydrophilic spacer was EG, TEG, PEG 600, PEG 1000, PEG 2000, or PEG 4000. The sample names respectively assigned for these were "EG-NHS", "TEG-NHS", "PEG 600-NHS", "PEG 1000-NHS", "PEG 2000-NHS", and "PEG 4000-NHS". It is found that the amount of BSA immobilized through covalent bonding decreased with increase in molecular weight of the PEG. This suggests that the surface density of active esters decreased with increase in the molecular weight of the PEG.

From the results given in FIGS. 2 and 3, the activity per molecule of immobilized HRP is obtained using the defining equation given below.

$$\text{Activity per molecule of } HRP = \frac{\text{Absorbance }(HRP \to EA) - \text{Absorbance }(EA \to HRP)}{\text{Absorbance }(BSA \to EA) - \text{Absorbance }(EA \to BSA)}$$

Here, it is assumed that the amount of HRP immobilized matches with the amount of BSA immobilized; this assumption is rational. As is clear from FIG. 4, the activity per molecule of HRP immobilized increased with increase in the molecular weight of the PEG. This is most probably because, with increase in molecular weight of the PRG, the conformational mobility of HRP increased or the surface density of the active ester became suitably low, which allowed retention of HRP activity.

EXAMPLE 2

Figure 5:
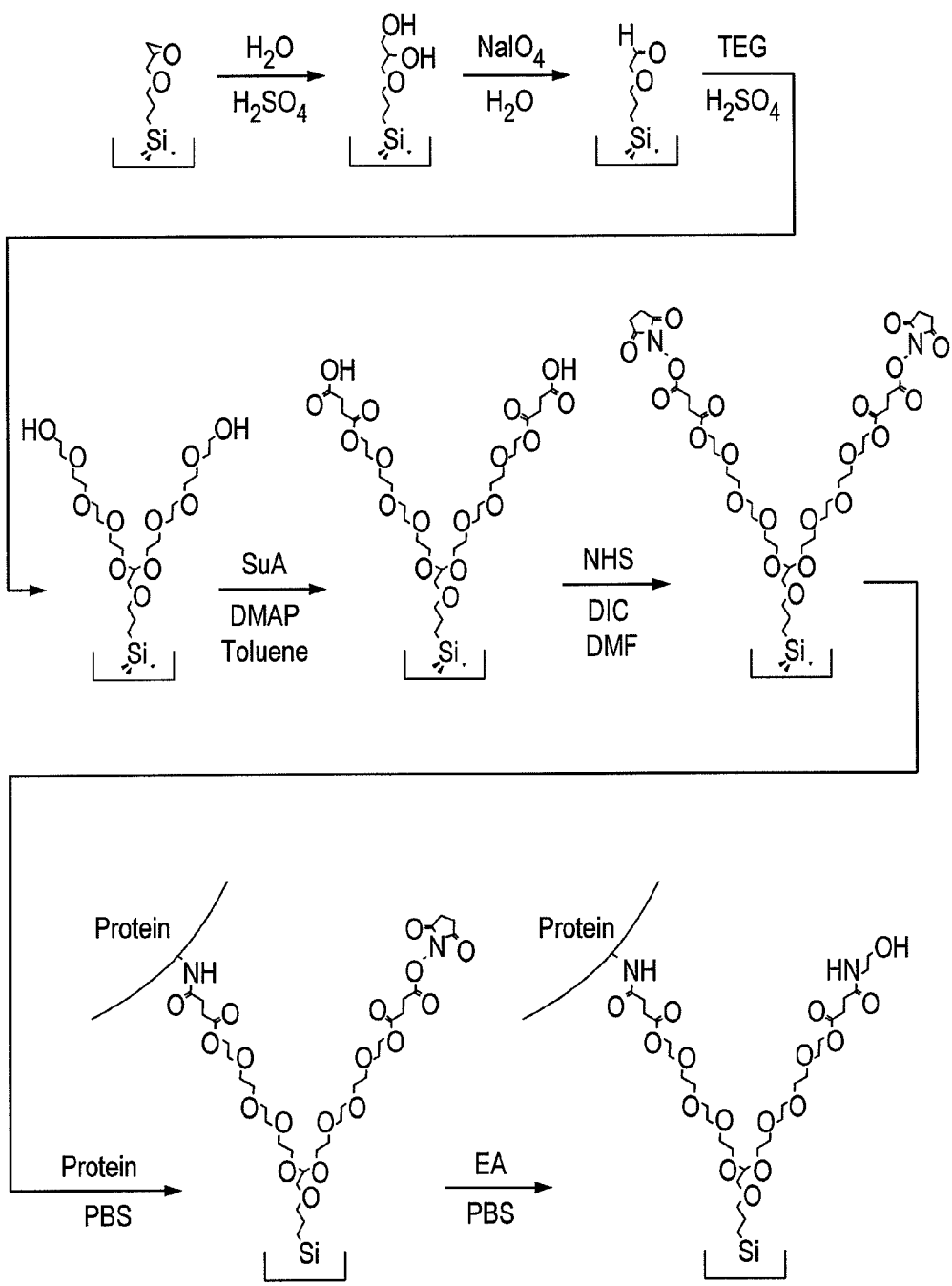
FIG. 5 is one embodiment of the present invention, which has a step of introducing aldehyde groups on a glass surface.

The Example shown in FIG. 5 comprises a step of introducing aldehyde groups on a glass surface, a step of covalent bonding of TEG to the aldehyde group, a step of reacting anhydrous succinic acid with the hydroxyl groups present at the free ends of the TEG to form carboxyl groups, a step of converting the carboxyl groups into active esters, a step of making a protein to act on active esters, and a step of inactivating the unreacted active esters using ethanolamine. The specific procedures used are described below.

39 g of toluene, 450 µl of 3-glycidoxypropyltrimethoxysilane, and 900 µl of triethylamine were mixed, and a 10 cm square UV-cleansed glass substrate was immersed in it and shaken mildly for 20 hours at room temperature. After that, the substrate was washed with ethanol and water and nitrogen blow-dried. Epoxy groups were introduced on the glass surface by this procedure. In the next step, the substrate was immersed in dilute (10 mM) sulfuric acid and heated for 2 hour at 80° C. After this, the substrate was washed well with water and nitrogen blow-dried. By this operation, the epoxy groups were hydrolyzed and 1,2-diols were formed. Next, the substrate was immersed in 20 mM aqueous sodium periodate solution (Kanto Chemical), left standing for 15 minutes at room temperature, and washed with water. By this operation, the 1,2-diols underwent oxidative cleavage to form aldehyde groups. After that, the substrate was immersed in TEG containing catalytic amounts of concentrated sulfuric acid and heated for 1 hour at 80° C. The substrate was then washed well with water and nitrogen blow-dried. In this step, the TEG reacted with the aldehyde groups to form covalent bonds. Next, 100 mg of SuA and 120 mg DMAP were dissolved in 43 g of toluene, and the above substrate was immersed in it and heated for 1 hour at 80° C. The substrate was then washed with ethanol and water and nitrogen blow-dried. This step formed carboxyl groups on the free ends of the TEG. Next, 290 mg of NHS and 390 µl of DIC were dissolved in 47 g of DMF, and the substrate was immersed in it and heated for 1 hour at 80° C. After that, the substrate was washed with ethanol and water and nitrogen blow-dried. NHS groups were introduced at the free ends of the TEG by this operation. Lastly, the substrate was cut into pieces of size 25 mm×10 mm.

Figure 6:
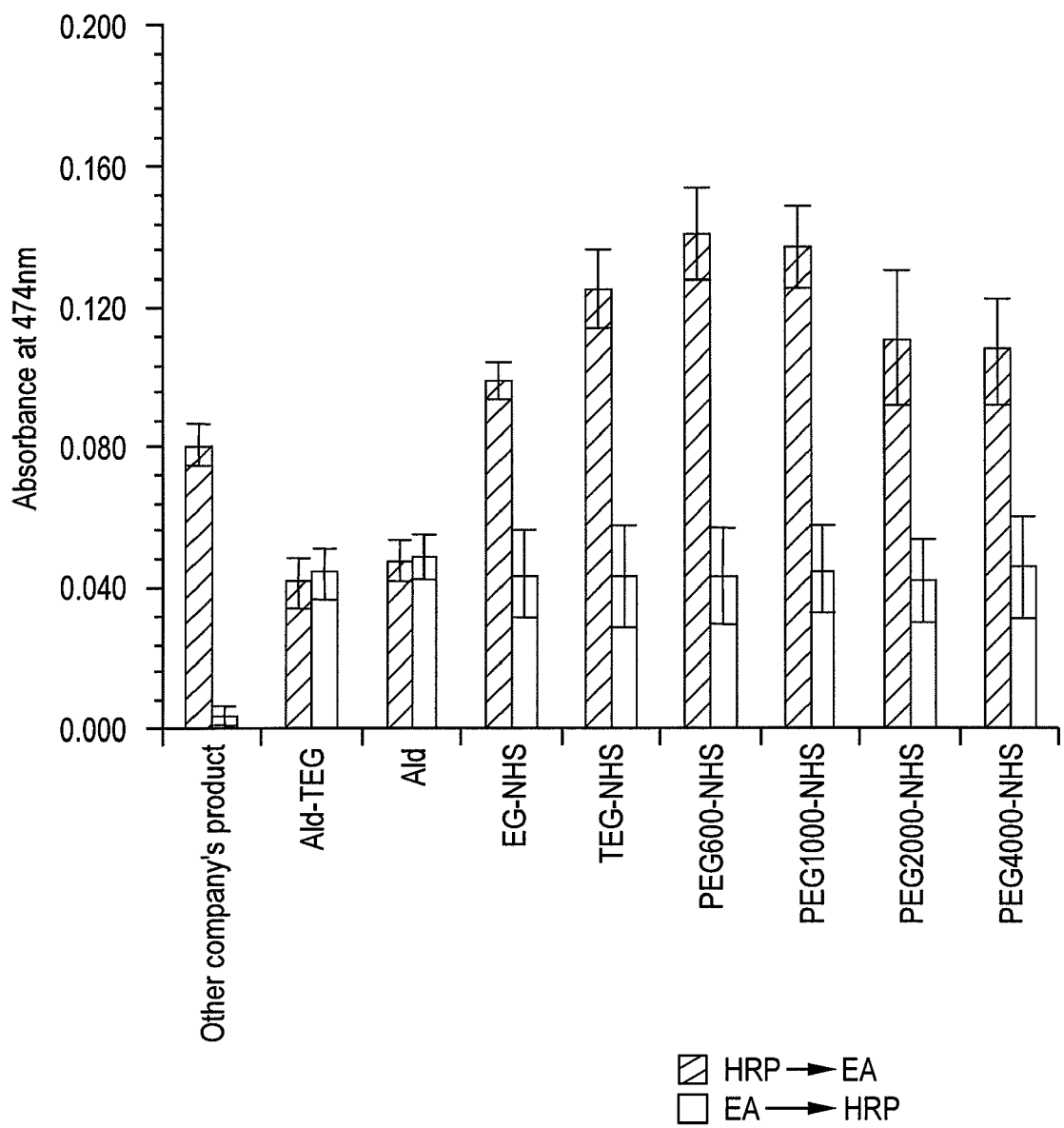
FIG. 6 is the result of measurement of activity of immobilized HRP in Example 2 (including the Comparative Examples).
Figure 7:
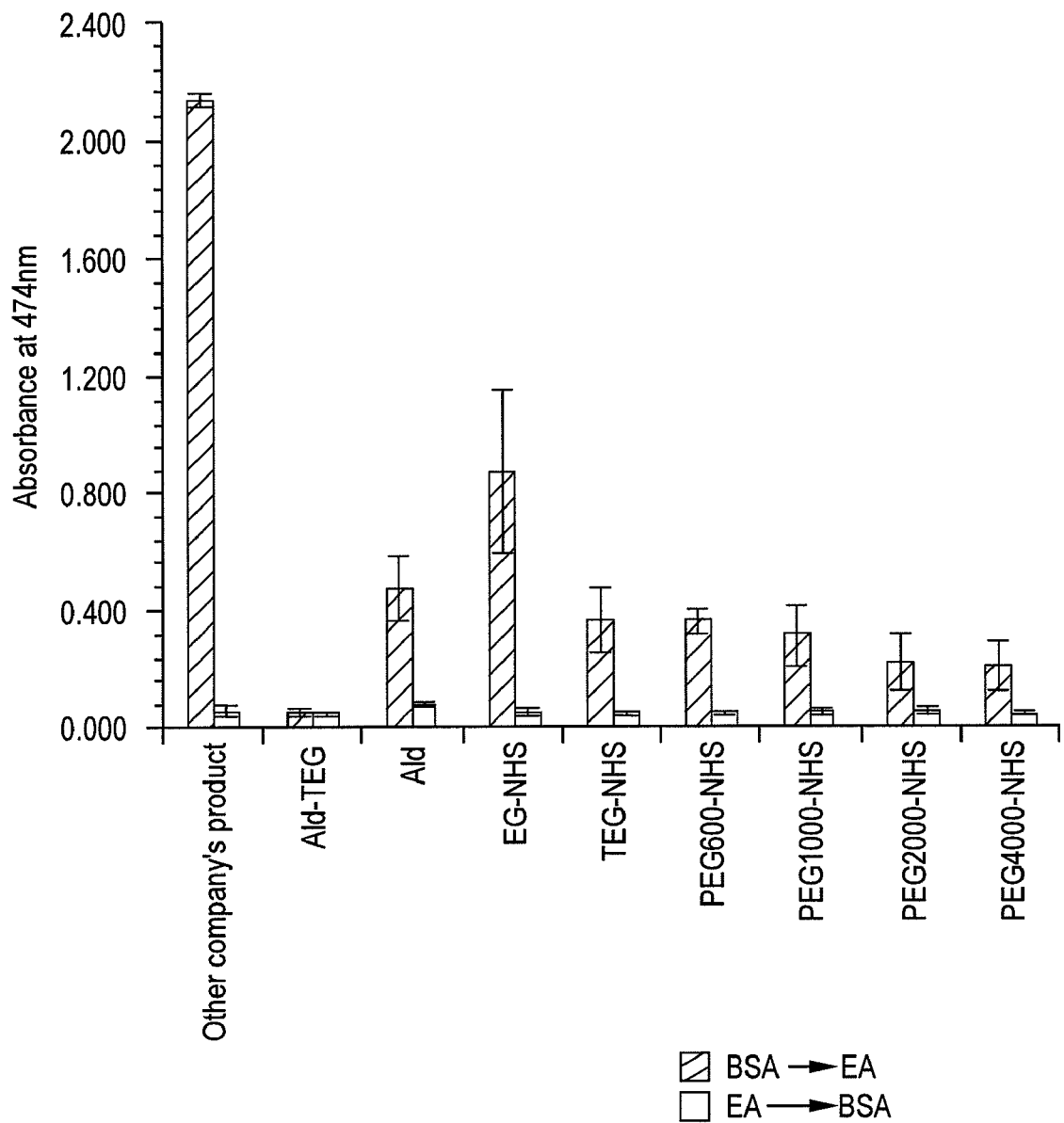
FIG. 7 is the result of measurement of the amount of immobilized BSA in Example 2 (including the Comparative Examples).
Figure 8:
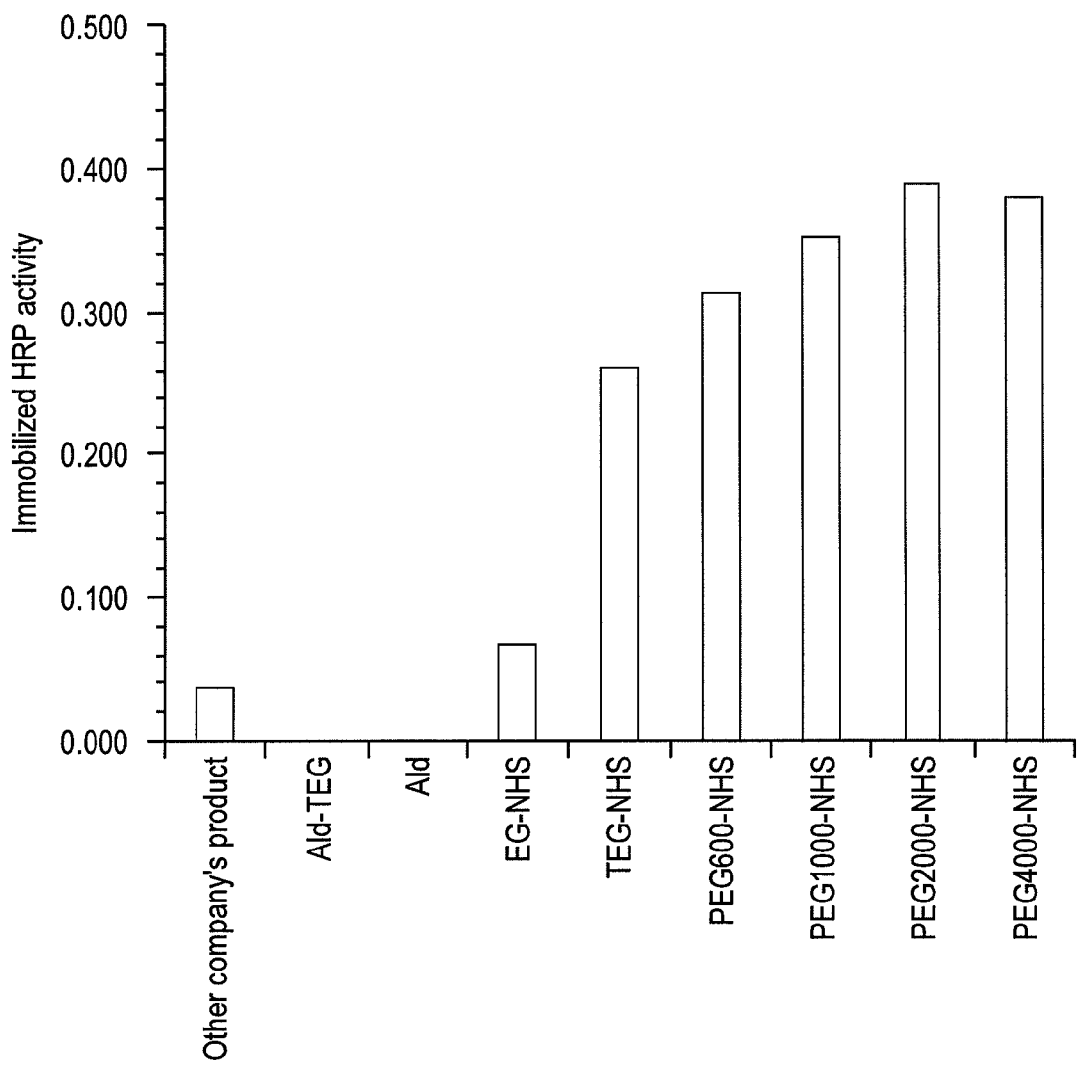
FIG. 8 is the activity per molecule of immobilized of HRP in Example 2 (including the Comparative Examples).

The activity of the immobilized HRP was then measured, and the amount of immobilized BSA was determined quantitatively as in Example 1. The results are shown in FIGS. 6 to 8. As in Example 1, enzymatic activity per molecule of immobilized HRP increased with increase in the molecular weight of PEG, but the activity was in general higher than in Example 1. The possible reason for this is described below. Firstly, in the case of the epoxy group base, hydroxyl groups of the epoxy rings also participate in immobilization of HRP. The HRP immobilized here is practically not via the hydrophilic spacer, and this could be reason for decrease in the activity of HRP. On the other hand, with aldehyde group base, 2 molecules of the hydrophilic compound react with each aldehyde group. So, theoretically, all the HRP is immobilized through the hydrophilic spacer. Therefore, the activity of the HRP is better retained on the surface of the carrier with aldehyde group base than on the surface of carriers with epoxy group base, it is believed.

COMPARATIVE EXAMPLE 1

Figure 4:
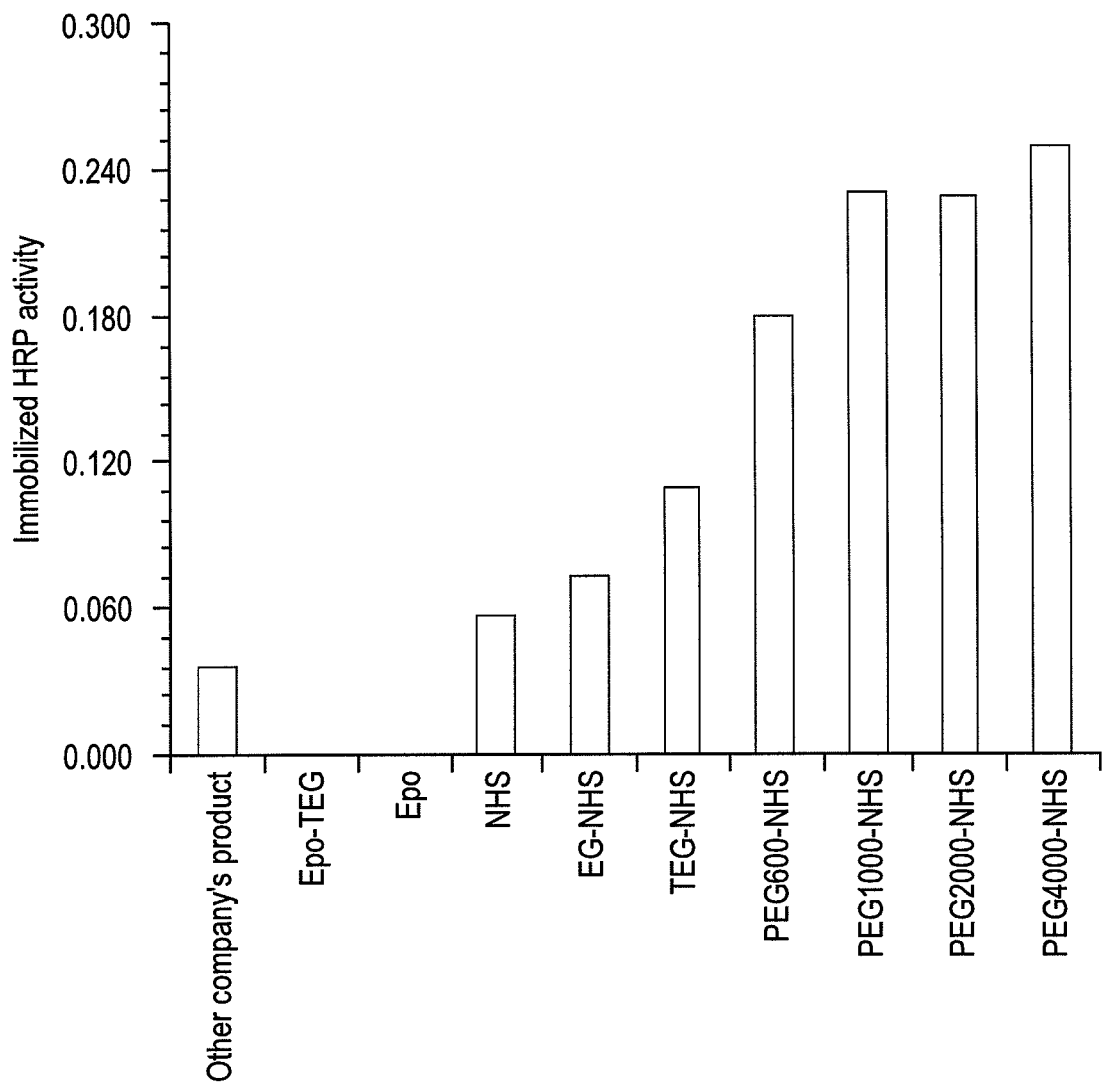
FIG. 4 is the activity per molecule of immobilized of HRP in Example 1 (including the Comparative Examples).

Comparative examples where no hydrophilic spacer was used are described below. Carriers having on their surface, epoxy groups, aldehyde groups, or NHS groups introduced using hydroxyl groups formed by hydrolysis of epoxy groups can be considered as substance immobilizing carriers without the hydrophilic spacers. The substance can be immobilized on the surface by covalent bonding in all these cases. In addition to this, carriers having a surface with TEG added to the epoxy group were also used as control samples. This carrier is known to definitely suppress nonspecific adsorption of proteins. The carriers were prepared as above. The results are given in FIGS. 2 to 4 and 6 to 8, along with the results of the examples. The samples were named as "Epo" for carriers having epoxy groups on the surface, "Ald" for carriers having aldehyde groups on the surface, "NHS" for carriers having NHS groups without hydrophilic spacer, on the surface and "Epo-TEG" for carriers having TEG-added epoxy groups on the surface. As can be seen from FIGS. 4 and 8, carriers having, on their surface, epoxy groups or aldehyde groups had absolutely no HRP activity in spite of the fact that a considerable amount of HRP had been immobilized through covalent bonding. The carrier having NHS groups on the surface without a hydrophilic spacer had markedly lower activity per molecule of immobilized HRP, compared to the case when there was a hydrophilic spacer (FIG. 4). Further, without exceptions, the carrier surfaces having hydrophilic spacers, suppressed the physical adsorption of BSA to a similar extent as in Epo-TEG. The above results demonstrated that the hydrophilic spacer in the present invention has the effect of retaining the activity of the protein, and the effect of suppressing nonspecific adsorption of substances.

COMPARATIVE EXAMPLE 2

The substance immobilizing carrier according to the technology described in Specification of U.S. Pat. No. 6,033,784 has been made into a commercial product. HRP and BSA were immobilized on the surface of this carrier as described above, and the activity and amount immobilized compared with those measured in the examples. The specific procedures used are described below.

100 µl of 1 mg/ml HRP solution (in a 1:1 mixture of a 100 mM aqueous sodium carbonate solution (pH 9.6) and glycerol) was added to the wells of a 96-well multi-well plate type Nunc Immobilizer™ Amino and incubated for 10 minutes at room temperature. By doing this, the electrophilic functional groups on the surface of the carrier reacted with the HRP, immobilizing it on the carrier surface. The insides of the wells were then washed three times with the washing buffer, brought into contact with 100 mM aqueous sodium carbonate solution (pH 9.6) containing 50 mM ethanolamine (EA), and incubated for 10 minutes at room temperature. This almost completely inactivated the unreacted electrophilic functional groups. After washing three times with the washing buffer, 100 µl of substrate solution was added to the wells, and the plate was incubated for 10 minutes at room temperature. Immediately after that, 100 µl of 1M sulfuric acid was added and the absorbance measured at 474 nm using the plate reader.

To subtract the contribution of physically adsorbed HRP from the measured value, the surface of the carrier whose electrophilic functional groups had been inactivated with ethanolamine was also evaluated in a similar way. Firstly, 100 µl of 50 mM ethanolamine (EA) was added to the wells of the above-described Nunc Immobilizer™ Amino, and the plate was incubated for 10 minutes at room temperature. By doing this, the electrophilic functional groups on the surface of the carrier were almost completely inactivated. Then, 100 µl of 1 mg/ml HRP solution was added and the plate incubated for 10 minutes at room temperature. This made the HRP to become physically adsorbed on the surface of the carrier without being immobilized. After washing three times with the washing buffer, 100 µl of the substrate solution was added to the wells and the plate incubated for 10 minutes at room temperature. Immediately after this, 100 µl of 1M sulfuric acid was added and the absorbance at 474 nm measured with the plate reader.

The above results are shown in FIGS. 2 to 4 and 6 to 8, along with the results of examples. The samples were designated as "Other company's product". Though some level of activity of immobilized HRP was detected in the other company's product, the levels were lower than in the carriers according to the present invention. On the other hand, the amount of BSA immobilized was far greater in the other company's product than in the present invention. However, the activity per molecule of immobilized HRP was much less in the other company's product than in the present invention. It thus became clear that the substance immobilizing carrier of the present invention retains the activity of proteins comparatively well.

EXAMPLE 3

To apply the present invention effectively, it is very important to use a suitable catalyst in the carboxyl group-forming step. The results of experiments on which the above statement is based are described below.

39 g of toluene, 450 µl of 3-glycidoxypropyltrimethoxysilane, and 900 µl of triethylamine were mixed, and a 10 cm square UV-cleansed glass substrate was immersed in it and shaken mildly for 20 hours at room temperature. After that, the substrate was washed with ethanol and water and nitrogen blow-dried. Epoxy groups were introduced on the glass surface by this operation. Next, the above substrate was immersed in TEG containing a catalytic amount of concentrated sulfuric acid and heated for 1 hour at 80° C. After this reaction, the substrate was washed well with water and nitrogen blow-dried. In this operation, the TEG reacted with epoxy groups to form covalent bonds. Then, after cutting the substrate to a suitable size, each piece was immersed in a different reaction solution (toluene solvent), namely, (1) SuA/without catalyst, (2) SuA/DMAP, (3) SuA/pyridine, (4) SuA/triethylamine, and (5) SuA/pyridine/triethylamine. Here, the concentration of SuA and the various catalysts was kept uniformly at 20 mM in all cases. After heating for 1 hour at 80° C., these substrates were washed with ethanol and water, and nitrogen blow-dried. By this operation, carboxyl groups were formed at the free ends of TEG with an efficiency determined by the type of catalyst used. Next, 290 mg of NHS and 390 µl of DIC were dissolved in 47 g of DMF, the five types of glass substrates were immersed in it, and heated for 1 hour at 80° C. After that, the substrates were washed with ethanol and water and nitrogen blow-dried. This operation converted the carboxyl groups into NHS groups. Finally, the 5 types of substrates were immersed in an ethanol solution of octylamine (OA, Wako Pure Chemical Industries) (50 mM) and left standing for 10 minutes at room temperature. After that, the substrates were washed with ethanol and water and nitrogen blow-dried. This procedure immobilized the octylamine on (some of) the free terminals of TEG. In the course of the above-described series of chemical reactions, the water contact angle of the 5 types of substrate changed as shown in Table 3. Here, the larger the water contact angle after the reaction with the octylamine, the higher was the efficiency of the reaction between the TEG and SuA before that. According to this result, it became clear that catalytic efficiency was in the order pyridine<triethylamine<DMAP, and that a satisfactory reaction rate and yield could be achieved only when DMAP was used.

TABLE 3

| Catalyst | Reactant | | | |
| --- | --- | --- | --- | --- |
| | TEG | SuA/catalyst | NHS/DIC | OA |
| None | 30.2 | 30.0 | 29.1 | 31.4 |
| 4-dimethylaminopyridine | 31.7 | 36.1 | 42.2 | 69.2 |
| Pyridine | 31.4 | 30.4 | 30.1 | 34.3 |
| Triethylamine | 31.4 | 32.3 | 35.9 | 56.4 |
| Triethylamine + pyridine | 31.2 | 32.7 | 35.1 | 58.0 |

EXAMPLE 4

To apply the present invention effectively, a suitable method needs to be selected at the time of introduction of functional groups on a support. For example, when functional groups are introduced on a glass surface using a general-purpose silane coupling agent, the performance of the substance immobilizing carrier differs largely depending on the use of an immersion method or the use of a sol-gel method. Example showing the evidence thereof is described below.

Functional groups were introduced on a glass surface by the immersion method as follows. Firstly, 39 g of toluene (Junsei Chemical), 450 µl of 3-glycidoxypropyltrimethoxysilane (TSL8350, GE Toshiba Silicone), and 900 µl of triethylamine (Wako Pure Chemical Industries) were mixed, and a 10 cm square UV-cleansed glass substrate (NA35, NH Technoglass) was immersed in it and shaken mildly for 20 hours at room temperature. After that, the substrate was washed with ethanol and water and nitrogen blow-dried. On the other hand, functional groups were introduced on a glass surface by the sol-gel method as follows. Firstly, 2205 µl of 3-glycidoxypropyltrimethoxysilane (TSL8350, GE Toshiba Silicone) and 480 µl of 0.005 N hydrochloric acid were mixed and stirred for 1 hour. This was diluted with isopropyl alcohol to prepare a 0.25% sol solution. A glass substrate (NA35, NH Technoglass) was coated with this by spin coating. The number of revolutions was set at 1000 rpm, and the revolution time at 3 seconds. After drying for a while, the substrate was heated for 20 minutes in an oven at 80° C. Each of these glass substrates silane-treated by the different methods was immersed in TEG (Kanto Chemical) containing a catalytic amount of concentrated sulfuric acid and heated for 1 hour at 80° C. After this reaction, the substrate was washed well with water and nitrogen blow-dried. Next, 100 mg of anhydrous succinic acid (SuA, Kanto Chemical) and 120 mg of 4-dimethylaminopyridine (DMAP, Wako Pure Chemical Industries) were dissolved in 43 g of toluene, the above substrate immersed in it, and heated for 1 hour at 80° C. After that, the substrate was washed with ethanol and water, and nitrogen blow-dried. Next, 290 mg of N-hydroxysuccinimide (NHS, Wako Pure Chemical Industries) and 390 µl of N,N'-diisopropylcarbodiimide (DIC, Wako Pure Chemical Industries) were dissolved in 47 g of N,N'-dimethylformamide (DMF, Kanto Chemical), and the substrate was immersed in it and heated for 1 hour at 80° C. The substrate was washed with ethanol and water, and nitrogen blow-dried. After that, the substrate was cut into pieces of size 25 mm×10 mm. Two substance immobilizing carriers differing only in the method of applying the silane coupling agent were obtained by the above-described procedures.

Figure 9:
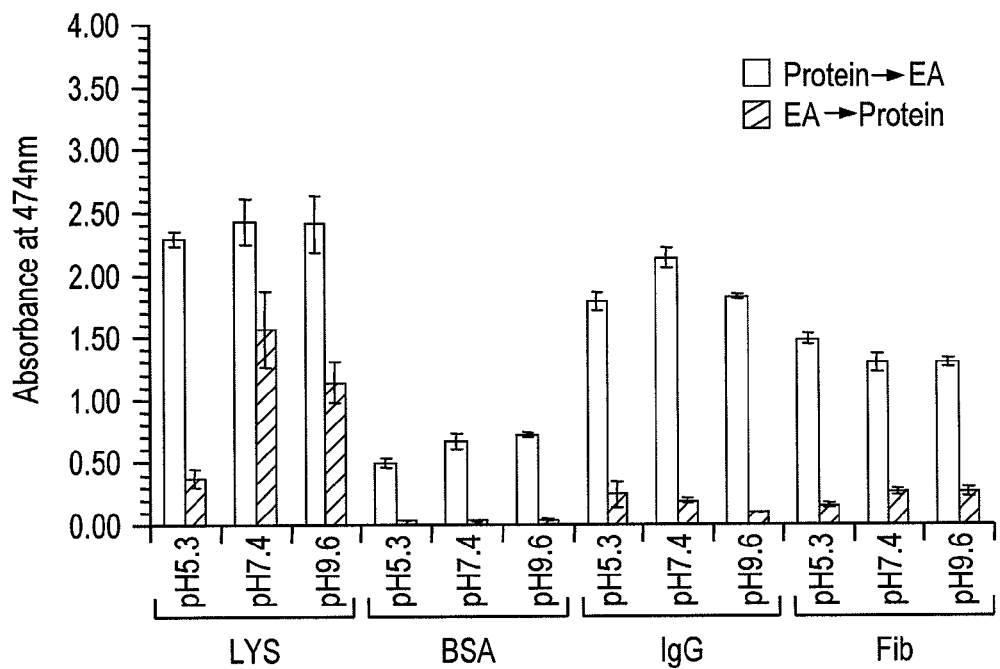
FIG. 9 is the result of evaluation in Example 4 (comparison of an immersion method with a sol-gel method).
Figure 9:
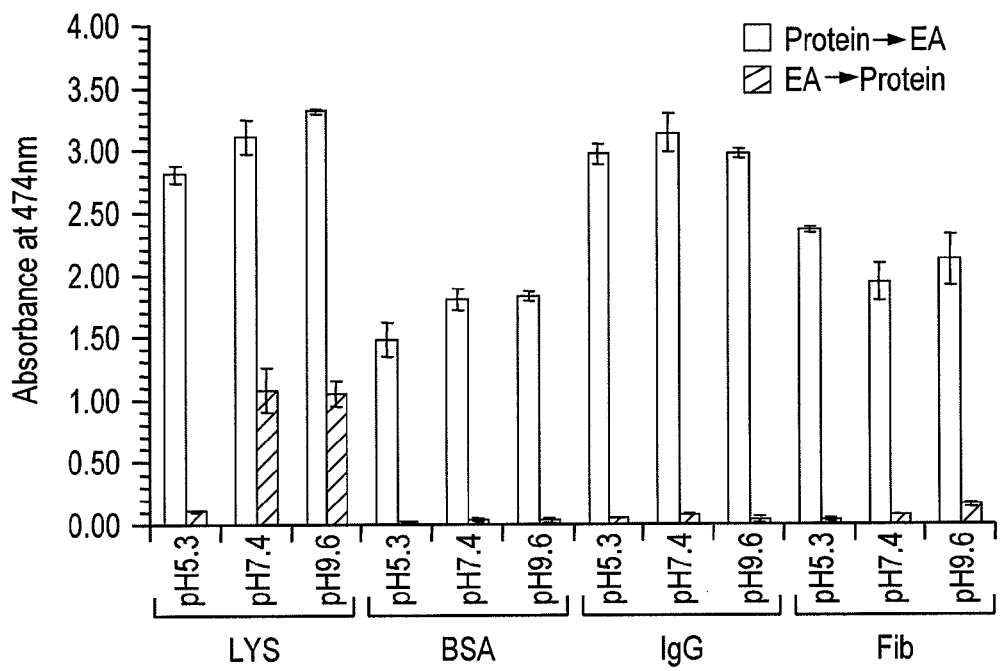

The amount of protein immobilized on these carriers and the amount of physical adsorption after inactivation were evaluated by ELISA. Lysozyme (Lys, Wako Pure Chemical Industries), BSA, anti-BSA antibody (IgG, ROCKLAND), and fibrinogen (Fib, Wako Pure Chemical Industries) were used as the protein. Firstly, 0.5 mg/ml protein solution was adjusted to three pHs (5.3, 7.4, and 9.6). These were separately brought into contact with each of the above-described two carriers and incubated for 10 minutes at room temperature. This allowed the reaction between the active esters on the surface of the carrier and the protein to occur, and the protein to get immobilized on the surface of the carrier. The surface of the carrier was then washed three times with the washing buffer, brought into contact with 50 mM ethanolamine (EA), and incubated for 10 minutes at room temperature. By doing this, the unreacted active esters were almost completely inactivated. The 0.5 mg/ml protein solutions were also separately brought into contact with each of the carriers inactivated with ethanolamine in a similar manner. After washing three times with the washing buffer, the surface of each carrier was bound to a primary antibody against each protein and subsequently bound to HRP-labeled secondary antibody (invitrogen). After washing with the washing buffer, 200 µl of the substrate solution was dropped on the surface of each carrier, and it was incubated for 10 minutes at room temperature. Immediately after that, 100 µl of the substrate solution was sampled, and transferred to a 96-well multi-well plate. 100 µl of 1 M concentrated sulfuric acid was added to this and the absorbance at 474 nm was measured with the plate reader. The result is shown in FIG. 9. For all the proteins, the significantly larger amount immobilized and the smaller amount of physical adsorption after inactivation were obtained in the carriers prepared by the sol-gel method than in the carriers prepared by the immersion method. This result demonstrated that the present invention can be applied suitably by introducing functional groups on a support by a sol-gel method.

EXAMPLE 5

It is preferable that nonspecific adsorption of proteins does not occur after inactivating the unreacted active esters. However, the effect differs largely depending on reagents used. The most effective inactivating reagent in the present invention is diglycolamine. Example showing the evidence thereof is described below.

Figure 10:
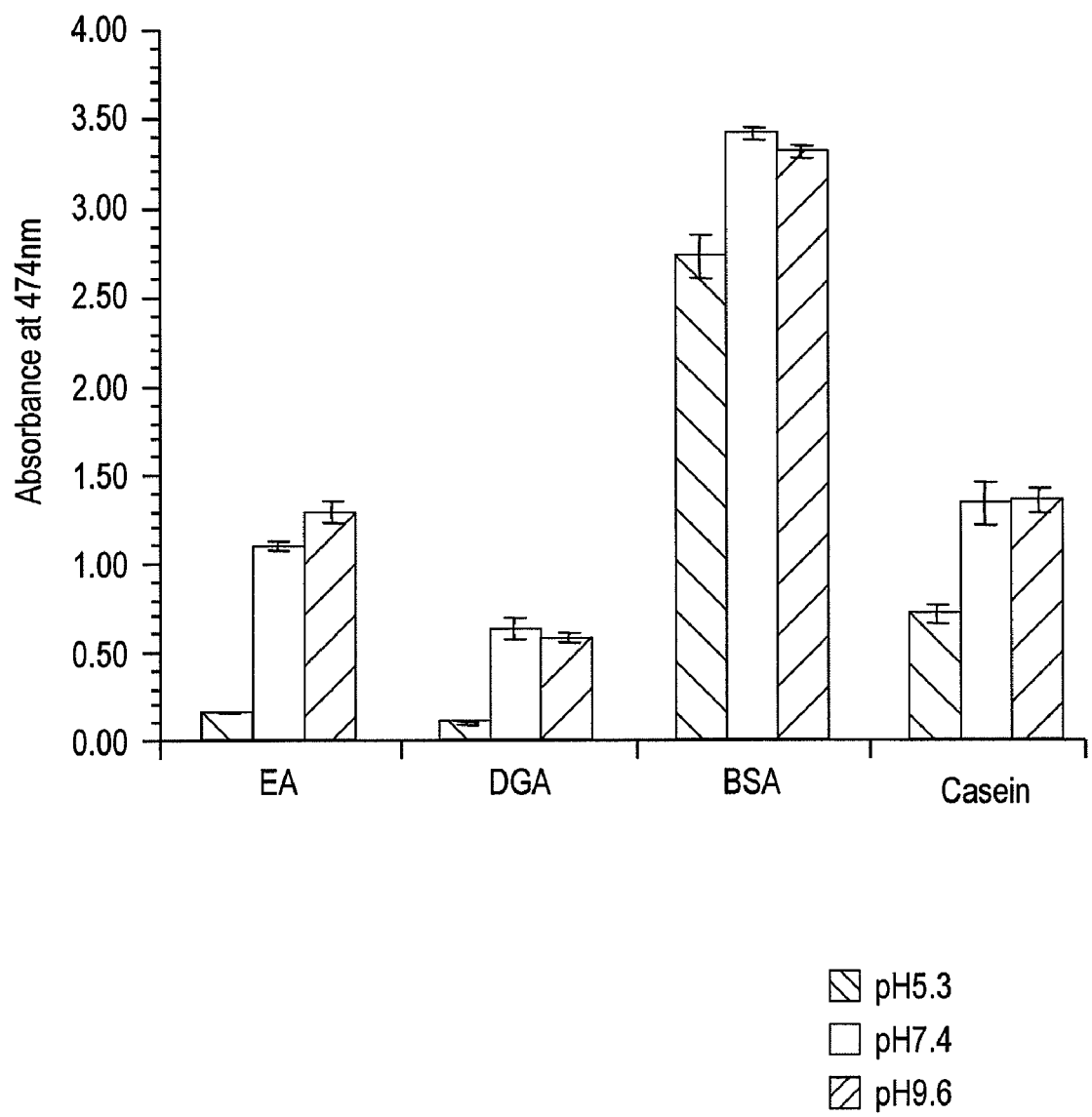
FIG. 10 is the result of evaluation in Example 5 (comparison of inactivating reagents).

Firstly, as described in Example 4, epoxy groups were introduced on a glass surface by the sol-gel method. Next, 50 mg of anhydrous succinic acid (SuA, Kanto Chemical) and 60 mg of 4-dimethylaminopyridine (DMAP, Wako Pure Chemical Industries) were dissolved in 43 g of toluene, the above substrate immersed in it, and heated for 1 hour at 80° C. After that, the substrate was washed with ethanol and water, and nitrogen blow-dried. Next, 58 mg of N-hydroxysuccinimide (NHS, Wako Pure Chemical Industries) and 78 µl of N,N'-diisopropylcarbodiimide (DIC, Wako Pure Chemical Industries) were dissolved in 43 g of toluene (Junsei Chemical), and the substrate was immersed in it and heated for 1 hour at 80° C. The substrate was washed with ethanol and water, and nitrogen blow-dried. After that, the substrate was cut into pieces of size 25 mm×10 mm. This substrate was treated with each inactivating reagent and then brought into contact with 0.5 mg/ml lysozyme (Wako Pure Chemical Industries). The amount of physical adsorption was evaluated by ELISA. The inactivating reagents used were four, ethanolamine (EA), diglycolamine (DGA), BSA, and casein (Hammarsten grade, Wako Pure Chemical Industries). As a result, the smallest amount of physical adsorption was obtained in the carrier inactivated with diglycolamine (FIG. 10). BSA, which is used most generally for the purpose of preventing nonspecific adsorption of proteins, was not effective in the present invention. This result demonstrated that the present invention is applied suitably by inactivating active esters with diglycolamine.

What is claimed is:
1. A method of producing a substance immobilizing carrier having a hydrophilic spacer, which comprises:
    a functional group-introducing step wherein a functional group is introduced on a surface of a support;
    a hydrophilic compound-binding step wherein a hydrophilic compound having a hydroxyl group and having a binding group that can bind with the functional group, is bound to the functional group through bonding between the functional group and the binding group; and
    a carboxyl group-forming step wherein an ester with a carboxyl group originating from a cyclic anhydride is formed through a ring-opening half-esterification between the cyclic acid anhydride and the hydroxyl group on the bound hydrophilic compound.

2. The method according to claim 1 wherein the ring-opening half esterification in the carboxyl group-forming step is carried out using 4-dimethylaminopyridine as a catalyst.

3. The method according to claim 1 wherein the method further comprises an active esterification step in which the carboxyl group formed in the carboxyl group-forming step is converted into an active ester.

4. The method according to claim 1 wherein the functional group introduced on the support is at least one selected from the group consisting of an epoxy group, an aldehyde group, and an amino group.

5. The method according to claim 4, wherein the functional group-introducing step comprises a step in which a silane coupling agent having the functional group is applied to the surface of the support by a sol-gel method.

6. The method according to claim 1 wherein the hydrophilic compound is at least one selected from the group consisting of ethylene glycol, polyethylene glycol, and a copolymer of ethylene glycol and propylene glycol.

7. The method according to claim 1 wherein the cyclic acid anhydride is anhydrous succinic acid or anhydrous glutaric acid.

8. The method according to claim 1 wherein
the functional group introduced on the support is an epoxy group,
the hydrophilic compound is at least one selected from the group consisting of ethylene glycol, polyethylene glycol, and a copolymer of ethylene glycol and propylene glycol,
the cyclic acid anhydride is anhydrous succinic acid or anhydrous glutaric acid, and
if the method further has the active esterification step, the active ester is N-hydroxysuccinimide ester.

9. The method according to claim 1 wherein
the functional group introduced on the support is an aldehyde group,
the hydrophilic compound is at least one selected from the group consisting of ethylene glycol, polyethylene glycol, and a copolymer of ethylene glycol and propylene glycol,
the cyclic acid anhydride is anhydrous succinic acid or anhydrous glutaric acid, and
if the method further has the active esterification step, the active ester is N-hydroxysuccinimide ester.

\* \* \* \* \*